US010472626B2

(12) United States Patent
Sampath

(10) Patent No.: US 10,472,626 B2
(45) Date of Patent: *Nov. 12, 2019

(54) MODIFIED ANTIMIR-138 OLIGONUCLEOTIDES

(71) Applicant: AGENCY FOR SCIENCE, TECHNOLOGY AND RESEARCH, Singapore (SG)

(72) Inventor: Prabha Sampath, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/500,022

(22) PCT Filed: Jul. 31, 2015

(86) PCT No.: PCT/SG2015/050245
§ 371 (c)(1),
(2) Date: Jan. 27, 2017

(87) PCT Pub. No.: WO2016/018193
PCT Pub. Date: Feb. 4, 2016

(65) Prior Publication Data
US 2017/0260526 A1 Sep. 14, 2017

(30) Foreign Application Priority Data

Jul. 31, 2014 (SG) .............................. 10201404535S

(51) Int. Cl.
*C12N 15/11* (2006.01)
*C12N 15/113* (2010.01)
*A61K 31/7088* (2006.01)

(52) U.S. Cl.
CPC ........ *C12N 15/113* (2013.01); *A61K 31/7088* (2013.01); *C12N 2310/113* (2013.01); *C12N 2310/315* (2013.01); *C12N 2310/321* (2013.01); *C12N 2310/3231* (2013.01); *C12N 2320/51* (2013.01)

(58) Field of Classification Search
CPC .............. C12N 15/113; C12N 2310/11; C12N 2310/141; C12N 15/11; C12N 2310/341; C12N 2310/113; C12N 2310/344; C12N 2310/321; C12N 2310/322; C12N 2310/315

See application file for complete search history.

(56) References Cited

U.S. PATENT DOCUMENTS

| 2005/0261218 A1* | 11/2005 | Esau | C12N 15/111 514/44 A |
|---|---|---|---|
| 2007/0049547 A1* | 3/2007 | Esau | C12N 15/113 514/44 A |
| 2010/0004320 A1* | 1/2010 | Elmen | C12N 15/113 514/44 R |
| 2010/0298410 A1* | 11/2010 | Obad | C12N 15/111 514/44 A |
| 2013/0281514 A1 | 10/2013 | Sampath | |
| 2014/0194491 A1 | 7/2014 | Kassem et al. | |
| 2015/0368642 A1* | 12/2015 | Albaek | A61K 47/64 514/44 A |

FOREIGN PATENT DOCUMENTS

| WO | WO 2007/112754 A2 | 10/2007 | |
|---|---|---|---|
| WO | WO 2012/087242 | 6/2012 | |
| WO | WO-2012087242 A1 * | 6/2012 | ........... C12N 15/113 |
| WO | WO 2012/175357 | 12/2012 | |

OTHER PUBLICATIONS

Siegel et al., A functional screen implicates microRNA-138-dependent regulation of the depalmitoylation enzyme ATP1 in dendritic spine morphogenesis, 2009, Nature Cell Biology, vol. 11, pp. 705-716.*
Banergee et al., A coordinated local translational control point at the synapse involving relief from silencing and MOV10 degradation, 2009, Neuron, vol. 64, pp. 871-884.*
Jin et al., Molecular characterization of the microRNA-138-fos-like antigen 1 (FOSL1) regulatory module in squamous cell carcinoma, 2011, Journal of Biological Chemistry, vol. 286, pp. 40104-40109.*
Ramachandran et al., A microRNA network regulates expression and biosynthesis of wild-type and deltaF508 mutant cystic fibrosis transmembrane conductance regulator, 2012, PNAS, vol. 109, pp. 13362-13367.*
Krützfeldt et al., Silencing of microRNAs in vivo with 'antagomirs', Nature, vol. 438, pp. 685-689. (Year: 2005).*
PCT International Preliminary Report on Patentability (Chapter I of the Patent Cooperation Treaty), 5 pgs (dated Jan. 31, 2017).
PCT Notification of Transmittal of the International Search Report and the Written Opinion of the International Searching Authority, or the Declaration for PCT Counterpart Application No. PCT/SG2015/050245, 11 pp., (dated Oct. 16, 2015).
Martin J. Søe, et al., "A Sensitive Alternative for MicroRNA in Situ Hybridizations Using Probes of 2'-O-Methyl RNA + LNA", Journal of Histochemistry & Cytochemistry, vol. 59, No. 7, pp. 661-672, (2011).
Tilde Eskildsen, et al., "MicroRNA-138 Regulates Osteogenic Differentiation of Human Stromal (Mesenchymal) Stem Cells in Vivo", PNAS, vol. 108, No. 15, pp. 6139-6144, (Apr. 12, 2011).

(Continued)

*Primary Examiner* — Dana H Shin
(74) *Attorney, Agent, or Firm* — Womble Bond Dickinson (US) LLP

(57) ABSTRACT

Disclosed is a modified oligonucleotide capable of reducing or inhibiting one or more activities miR-138. The modified oligonucleotide may comprise at least one locked nucleic acid (LNA) and wherein the oligonucleotide is substantially complementary to a nucleotide sequence of miR-138. Also disclosed are pharmaceutical compositions comprising the oligonucleotides, methods of using the oligonucleotides and uses thereof.

3 Claims, 18 Drawing Sheets
Specification includes a Sequence Listing.

(56) References Cited

OTHER PUBLICATIONS

Zhonghan Li, et al., "Therapeutic Targeting of MicroRNAs: Current Status and Future Challenges", Nature Reviews Drug Discovery, vol. 13, pp. 622-638, (Aug. 2014).
Jan Stenvang, et al., "Inhibition of MicroRNA Function by AntimiR Oligonucleotides", Silence, vol. 3, No. 1, pp. 1-17, (2012).
Supplementary European Search Report dated Dec. 12, 2017, EP Application No. 15826336.
Soe, et al., "A Sensitive Alternative for MicroRNA in Situ Hybridizations Using Probes of '-O-Methyl RNA+ LNA", Journal of Histochemistry & Cytochemistry, vol. 59, No. 7, 2011, pp. 661-672.
Yan, et al., "Non-viral oligonucleotide antimiR-138 delivery to mesenchymal stem cell sheets and the effect on osteogenesis", Biomaterials, vol. 35, 2014, pp. 7734-7749.
Li, et al., "Therapeutic targeting of microRNAs: current status and future challenges", Nature Reviews, vol. 13, Aug. 2014, pp. 622-638.
Extended European Search Report dated Dec. 19, 2017, EP Application No. 15826336.8.
Bernardo, et al., "A MicroRNA Guide for Clinicians and Basic Scientists: Background and Experimental Techniques", Heart, Lung and Circulation, 2012, vol. 21, pp. 131-142.

\* cited by examiner

A)

B)

C)

A)

B)

C)

A)

B)

A)

B)

SEQUENCE LISTING

<160> NUMBER OF SEQ ID NOS: 13

<210> SEQ ID NO 1
<211> LENGTH: 23
<212> TYPE: DNA
<213> ORGANISM: Homo sapiens

<400> SEQUENCE: 1
agctggtgtt gtgaatcagg ccg                                                  23

<210> SEQ ID NO 2
<211> LENGTH: 23
<212> TYPE: DNA
<213> ORGANISM: ARTIFICIAL SEQUENCE
<220> FEATURE:
<223> OTHER INFORMATION: ANTI-MIR 138

<400> SEQUENCE: 2
cggccugaut cacaacacca gcu                                                  23

<210> SEQ ID NO 3
<211> LENGTH: 23
<212> TYPE: DNA
<213> ORGANISM: ARTIFICIAL SEQUENCE
<220> FEATURE:
<223> OTHER INFORMATION: ANTI-MIR 138

<400> SEQUENCE: 3
cggccugauu cacaacacca gcu                                                  23

<210> SEQ ID NO 4
<211> LENGTH: 11
<212> TYPE: DNA
<213> ORGANISM: ARTIFICIAL SEQUENCE
<220> FEATURE:
<223> OTHER INFORMATION: ANTI-MIR-138

<400> SEQUENCE: 4
acaacaccag c                                                               11

<210> SEQ ID NO 5
<211> LENGTH: 11
<212> TYPE: DNA
<213> ORGANISM: ARTIFICIAL SEQUENCE
<220> FEATURE:
<223> OTHER INFORMATION: AMO_138_11_CAP_PS OR ANTI-MIR138-4
<220> FEATURE:
<221> NAME/KEY: MISC_FEATURE
<222> LOCATION: (1)..(11)
<223> OTHER INFORMATION: MODIFIED WITH LOCKED NUCLEIC ACID MODIFICATION
<220> FEATURE:
<221> NAME/KEY: MISC_FEATURE
<222> LOCATION: (1)..(2)
<223> OTHER INFORMATION: MODIFIED WITH PHOSPHOROTHIOATE LINKAGE
<220> FEATURE:
<221> NAME/KEY: MISC_FEATURE
<222> LOCATION: (10)..(11)
<223> OTHER INFORMATION: MODIFIED WITH PHOSPHOROTHIOATE LINKAGE

<400> SEQUENCE: 5
acaacaccag c                                                               11

<210> SEQ ID NO 6
<211> LENGTH: 11
<212> TYPE: DNA
<213> ORGANISM: ARTIFICIAL SEQUENCE
<220> FEATURE:
<223> OTHER INFORMATION: AMO_CONTROL_11_CAP_PS

```
<220> FEATURE:
<221> NAME/KEY: MISC_FEATURE
<222> LOCATION: (1)..(11)
<223> OTHER INFORMATION: MODIFIED WITH LOCKED NUCLEIC ACID MODIFICATION
<220> FEATURE:
<221> NAME/KEY: MISC_FEATURE
<222> LOCATION: (1)..(2)
<223> OTHER INFORMATION: MODIFIED WITH PHOSPHOROTHIOATE LINKAGE
<220> FEATURE:
<221> NAME/KEY: MISC_FEATURE
<222> LOCATION: (10)..(11)
<223> OTHER INFORMATION: MODIFIED WITH PHOSPHOROTHIOATE LINKAGE

<400> SEQUENCE: 6
caaacaccga c                                                           11

<210> SEQ ID NO 7
<211> LENGTH: 23
<212> TYPE: DNA
<213> ORGANISM: ARTIFICIAL SEQUENCE
<220> FEATURE:
<223> OTHER INFORMATION: AMO_138_23
<220> FEATURE:
<221> NAME/KEY: MISC_FEATURE
<222> LOCATION: (1)..(3)
<223> OTHER INFORMATION: MODIFIED WITH PHOSPHOROTHIOATE LINKAGE
<220> FEATURE:
<221> NAME/KEY: MISC_FEATURE
<222> LOCATION: (1)..(2)
<223> OTHER INFORMATION: MODIFIED WITH 2'-O-METHYLATION
<220> FEATURE:
<221> NAME/KEY: MISC_FEATURE
<222> LOCATION: (3)..(3)
<223> OTHER INFORMATION: MODIFIED WITH LOCKED NUCLEIC ACID MODIFICATION
<220> FEATURE:
<221> NAME/KEY: MISC_FEATURE
<222> LOCATION: (4)..(5)
<223> OTHER INFORMATION: MODIFIED WITH 2'-O-METHYLATION
<220> FEATURE:
<221> NAME/KEY: MISC_FEATURE
<222> LOCATION: (6)..(6)
<223> OTHER INFORMATION: MODIFIED WITH LOCKED NUCLEIC ACID MODIFICATION
<220> FEATURE:
<221> NAME/KEY: MISC_FEATURE
<222> LOCATION: (7)..(8)
<223> OTHER INFORMATION: MODIFIED WITH 2'-O-METHYLATION
<220> FEATURE:
<221> NAME/KEY: MISC_FEATURE
<222> LOCATION: (9)..(9)
<223> OTHER INFORMATION: MODIFIED WITH LOCKED NUCLEIC ACID MODIFICATION
<220> FEATURE:
<221> NAME/KEY: MISC_FEATURE
<222> LOCATION: (10)..(11)
<223> OTHER INFORMATION: MODIFIED WITH 2'-O-METHYLATION
<220> FEATURE:
<221> NAME/KEY: MISC_FEATURE
<222> LOCATION: (12)..(12)
<223> OTHER INFORMATION: MODIFIED WITH LOCKED NUCLEIC ACID MODIFICATION
<220> FEATURE:
<221> NAME/KEY: MISC_FEATURE
<222> LOCATION: (13)..(14)
<223> OTHER INFORMATION: MODIFIED WITH 2'-O-METHYLATION
<220> FEATURE:
<221> NAME/KEY: MISC_FEATURE
<222> LOCATION: (15)..(15)
<223> OTHER INFORMATION: MODIFIED WITH LOCKED NUCLEIC ACID MODIFICATION
<220> FEATURE:
<221> NAME/KEY: MISC_FEATURE
<222> LOCATION: (16)..(17)
<223> OTHER INFORMATION: MODIFIED WITH 2'-O-METHYLATION
<220> FEATURE:
<221> NAME/KEY: MISC_FEATURE
<222> LOCATION: (18)..(18)
<223> OTHER INFORMATION: MODIFIED WITH LOCKED NUCLEIC ACID MODIFICATION
<220> FEATURE:
<221> NAME/KEY: MISC_FEATURE
<222> LOCATION: (19)..(20)
```

<223> OTHER INFORMATION: MODIFIED WITH 2'-O-METHYLATION
<220> FEATURE:
<221> NAME/KEY: MISC_FEATURE
<222> LOCATION: (20)..(22)
<223> OTHER INFORMATION: MODIFIED WITH PHOSPHOROTHIOATE LINKAGE
<220> FEATURE:
<221> NAME/KEY: MISC_FEATURE
<222> LOCATION: (21)..(21)
<223> OTHER INFORMATION: MODIFIED WITH LOCKED NUCLEIC ACID MODIFICATION
<220> FEATURE:
<221> NAME/KEY: MISC_FEATURE
<222> LOCATION: (22)..(23)
<223> OTHER INFORMATION: MODIFIED WITH 2'-O-METHYLATION
<220> FEATURE:
<221> NAME/KEY: CHOLESTEROL_CAP
<222> LOCATION: (23)..(23)

<400> SEQUENCE: 7
cggcctgatu cacaacacca gcu                                        23

<210> SEQ ID NO 8
<211> LENGTH: 23
<212> TYPE: DNA
<213> ORGANISM: ARTIFICIAL SEQUENCE
<220> FEATURE:
<223> OTHER INFORMATION: AMO_CONTROL_23
<220> FEATURE:
<221> NAME/KEY: MISC_FEATURE
<222> LOCATION: (1)..(3)
<223> OTHER INFORMATION: MODIFIED WITH PHOSPHOROTHIOATE LINKAGE
<220> FEATURE:
<221> NAME/KEY: MISC_FEATURE
<222> LOCATION: (1)..(2)
<223> OTHER INFORMATION: MODIFIED WITH 2'-O-METHYLATION
<220> FEATURE:
<221> NAME/KEY: MISC_FEATURE
<222> LOCATION: (3)..(3)
<223> OTHER INFORMATION: MODIFIED WITH LOCKED NUCLEIC ACID MODIFICATION
<220> FEATURE:
<221> NAME/KEY: MISC_FEATURE
<222> LOCATION: (4)..(5)
<223> OTHER INFORMATION: MODIFIED WITH 2'-O-METHYLATION
<220> FEATURE:
<221> NAME/KEY: MISC_FEATURE
<222> LOCATION: (6)..(6)
<223> OTHER INFORMATION: MODIFIED WITH LOCKED NUCLEIC ACID MODIFICATION
<220> FEATURE:
<221> NAME/KEY: MISC_FEATURE
<222> LOCATION: (7)..(8)
<223> OTHER INFORMATION: MODIFIED WITH 2'-O-METHYLATION
<220> FEATURE:
<221> NAME/KEY: MISC_FEATURE
<222> LOCATION: (9)..(9)
<223> OTHER INFORMATION: MODIFIED WITH LOCKED NUCLEIC ACID MODIFICATION
<220> FEATURE:
<221> NAME/KEY: MISC_FEATURE
<222> LOCATION: (10)..(11)
<223> OTHER INFORMATION: MODIFIED WITH 2'-O-METHYLATION
<220> FEATURE:
<221> NAME/KEY: MISC_FEATURE
<222> LOCATION: (12)..(12)
<223> OTHER INFORMATION: MODIFIED WITH LOCKED NUCLEIC ACID MODIFICATION
<220> FEATURE:
<221> NAME/KEY: MISC_FEATURE
<222> LOCATION: (13)..(14)
<223> OTHER INFORMATION: MODIFIED WITH 2'-O-METHYLATION
<220> FEATURE:
<221> NAME/KEY: MISC_FEATURE
<222> LOCATION: (15)..(15)
<223> OTHER INFORMATION: MODIFIED WITH LOCKED NUCLEIC ACID MODIFICATION
<220> FEATURE:
<221> NAME/KEY: MISC_FEATURE
<222> LOCATION: (16)..(17)
<223> OTHER INFORMATION: MODIFIED WITH 2'-O-METHYLATION
<220> FEATURE:
<221> NAME/KEY: MISC_FEATURE
<222> LOCATION: (18)..(18)

-continued

```
<223> OTHER INFORMATION: MODIFIED WITH LOCKED NUCLEIC ACID MODIFICATION
<220> FEATURE:
<221> NAME/KEY: MISC_FEATURE
<222> LOCATION: (19)..(20)
<223> OTHER INFORMATION: MODIFIED WITH 2'-O-METHYLATION
<220> FEATURE:
<221> NAME/KEY: MISC_FEATURE
<222> LOCATION: (20)..(22)
<223> OTHER INFORMATION: MODIFIED WITH PHOSPHOROTHIOATE LINKAGE
<220> FEATURE:
<221> NAME/KEY: MISC_FEATURE
<222> LOCATION: (21)..(21)
<223> OTHER INFORMATION: MODIFIED WITH LOCKED NUCLEIC ACID MODIFICATION
<220> FEATURE:
<221> NAME/KEY: MISC_FEATURE
<222> LOCATION: (22)..(23)
<223> OTHER INFORMATION: MODIFIED WITH 2'-O-METHYLATION
<220> FEATURE:
<221> NAME/KEY: CHOLESTEROL_CAP
<222> LOCATION: (23)..(23)

<400> SEQUENCE: 8
ggcaatccaa cggaccutca ccu                                             23

<210> SEQ ID NO 9
<211> LENGTH: 23
<212> TYPE: DNA
<213> ORGANISM: ARTIFICIAL SEQUENCE
<220> FEATURE:
<223> OTHER INFORMATION: AMO_106_23
<220> FEATURE:
<221> NAME/KEY: MISC_FEATURE
<222> LOCATION: (1)..(3)
<223> OTHER INFORMATION: MODIFIED WITH PHOSPHOROTHIOATE LINKAGE
<220> FEATURE:
<221> NAME/KEY: MISC_FEATURE
<222> LOCATION: (1)..(5)
<223> OTHER INFORMATION: MODIFIED WITH 2'-O-METHYLATION
<220> FEATURE:
<221> NAME/KEY: MISC_FEATURE
<222> LOCATION: (6)..(6)
<223> OTHER INFORMATION: MODIFIED WITH LOCKED NUCLEIC ACID MODIFICATION
<220> FEATURE:
<221> NAME/KEY: MISC_FEATURE
<222> LOCATION: (7)..(7)
<223> OTHER INFORMATION: MODIFIED WITH 2'-O-METHYLATION
<220> FEATURE:
<221> NAME/KEY: MISC_FEATURE
<222> LOCATION: (8)..(8)
<223> OTHER INFORMATION: MODIFIED WITH LOCKED NUCLEIC ACID MODIFICATION
<220> FEATURE:
<221> NAME/KEY: MISC_FEATURE
<222> LOCATION: (9)..(9)
<223> OTHER INFORMATION: MODIFIED WITH 2'-O-METHYLATION
<220> FEATURE:
<221> NAME/KEY: MISC_FEATURE
<222> LOCATION: (10)..(10)
<223> OTHER INFORMATION: MODIFIED WITH LOCKED NUCLEIC ACID MODIFICATION
<220> FEATURE:
<221> NAME/KEY: MISC_FEATURE
<222> LOCATION: (11)..(11)
<223> OTHER INFORMATION: MODIFIED WITH 2'-O-METHYLATION
<220> FEATURE:
<221> NAME/KEY: MISC_FEATURE
<222> LOCATION: (12)..(12)
<223> OTHER INFORMATION: MODIFIED WITH LOCKED NUCLEIC ACID MODIFICATION
<220> FEATURE:
<221> NAME/KEY: MISC_FEATURE
<222> LOCATION: (13)..(13)
<223> OTHER INFORMATION: MODIFIED WITH 2'-O-METHYLATION
<220> FEATURE:
<221> NAME/KEY: MISC_FEATURE
<222> LOCATION: (14)..(14)
<223> OTHER INFORMATION: MODIFIED WITH LOCKED NUCLEIC ACID MODIFICATION
<220> FEATURE:
<221> NAME/KEY: MISC_FEATURE
<222> LOCATION: (15)..(15)
```

<223> OTHER INFORMATION: MODIFIED WITH 2'-O-METHYLATION
<220> FEATURE:
<221> NAME/KEY: MISC_FEATURE
<222> LOCATION: (16)..(16)
<223> OTHER INFORMATION: MODIFIED WITH LOCKED NUCLEIC ACID MODIFICATION
<220> FEATURE:
<221> NAME/KEY: MISC_FEATURE
<222> LOCATION: (17)..(17)
<223> OTHER INFORMATION: MODIFIED WITH 2'-O-METHYLATION
<220> FEATURE:
<221> NAME/KEY: MISC_FEATURE
<222> LOCATION: (18)..(18)
<223> OTHER INFORMATION: MODIFIED WITH LOCKED NUCLEIC ACID MODIFICATION
<220> FEATURE:
<221> NAME/KEY: MISC_FEATURE
<222> LOCATION: (19)..(23)
<223> OTHER INFORMATION: MODIFIED WITH 2'-O-METHYLATION
<220> FEATURE:
<221> NAME/KEY: MISC_FEATURE
<222> LOCATION: (20)..(22)
<223> OTHER INFORMATION: MODIFIED WITH PHOSPHOROTHIOATE LINKAGE
<220> FEATURE:
<221> NAME/KEY: CHOLESTEROL_CAP
<222> LOCATION: (23)..(23)

<400> SEQUENCE: 9
cuacctgcac uguaagcacu uuu                                            23

<210> SEQ ID NO 10
<211> LENGTH: 23
<212> TYPE: DNA
<213> ORGANISM: ARTIFICIAL SEQUENCE
<220> FEATURE:
<223> OTHER INFORMATION: AMO_138_23_1 OR ANTI-MIR138-1
<220> FEATURE:
<221> NAME/KEY: MISC_FEATURE
<222> LOCATION: (1)..(3)
<223> OTHER INFORMATION: MODIFIED WITH PHOSPHOROTHIOATE LINKAGE
<220> FEATURE:
<221> NAME/KEY: MISC_FEATURE
<222> LOCATION: (1)..(5)
<223> OTHER INFORMATION: MODIFIED WITH 2'-O-METHYLATION
<220> FEATURE:
<221> NAME/KEY: MISC_FEATURE
<222> LOCATION: (6)..(6)
<223> OTHER INFORMATION: MODIFIED WITH LOCKED NUCLEIC ACID MODIFICATION
<220> FEATURE:
<221> NAME/KEY: MISC_FEATURE
<222> LOCATION: (7)..(7)
<223> OTHER INFORMATION: MODIFIED WITH 2'-O-METHYLATION
<220> FEATURE:
<221> NAME/KEY: MISC_FEATURE
<222> LOCATION: (8)..(8)
<223> OTHER INFORMATION: MODIFIED WITH LOCKED NUCLEIC ACID MODIFICATION
<220> FEATURE:
<221> NAME/KEY: MISC_FEATURE
<222> LOCATION: (9)..(9)
<223> OTHER INFORMATION: MODIFIED WITH 2'-O-METHYLATION
<220> FEATURE:
<221> NAME/KEY: MISC_FEATURE
<222> LOCATION: (10)..(10)
<223> OTHER INFORMATION: MODIFIED WITH LOCKED NUCLEIC ACID MODIFICATION
<220> FEATURE:
<221> NAME/KEY: MISC_FEATURE
<222> LOCATION: (11)..(11)
<223> OTHER INFORMATION: MODIFIED WITH 2'-O-METHYLATION
<220> FEATURE:
<221> NAME/KEY: MISC_FEATURE
<222> LOCATION: (12)..(12)
<223> OTHER INFORMATION: MODIFIED WITH LOCKED NUCLEIC ACID MODIFICATION
<220> FEATURE:
<221> NAME/KEY: MISC_FEATURE
<222> LOCATION: (13)..(13)
<223> OTHER INFORMATION: MODIFIED WITH 2'-O-METHYLATION
<220> FEATURE:
<221> NAME/KEY: MISC_FEATURE
<222> LOCATION: (14)..(14)

```
<223> OTHER INFORMATION: MODIFIED WITH LOCKED NUCLEIC ACID MODIFICATION
<220> FEATURE:
<221> NAME/KEY: MISC_FEATURE
<222> LOCATION: (15)..(15)
<223> OTHER INFORMATION: MODIFIED WITH 2'-O-METHYLATION
<220> FEATURE:
<221> NAME/KEY: MISC_FEATURE
<222> LOCATION: (16)..(16)
<223> OTHER INFORMATION: MODIFIED WITH LOCKED NUCLEIC ACID MODIFICATION
<220> FEATURE:
<221> NAME/KEY: MISC_FEATURE
<222> LOCATION: (17)..(17)
<223> OTHER INFORMATION: MODIFIED WITH 2'-O-METHYLATION
<220> FEATURE:
<221> NAME/KEY: MISC_FEATURE
<222> LOCATION: (18)..(18)
<223> OTHER INFORMATION: MODIFIED WITH LOCKED NUCLEIC ACID MODIFICATION
<220> FEATURE:
<221> NAME/KEY: MISC_FEATURE
<222> LOCATION: (19)..(23)
<223> OTHER INFORMATION: MODIFIED WITH 2'-O-METHYLATION
<220> FEATURE:
<221> NAME/KEY: MISC_FEATURE
<222> LOCATION: (20)..(22)
<223> OTHER INFORMATION: MODIFIED WITH PHOSPHOROTHIOATE LINKAGE

<400> SEQUENCE: 10
cggcctgaut cacaacacca gcu                                             23

<210> SEQ ID NO 11
<211> LENGTH: 23
<212> TYPE: DNA
<213> ORGANISM: ARTIFICIAL SEQUENCE
<220> FEATURE:
<223> OTHER INFORMATION: AMO_CONTROL_23_1
<220> FEATURE:
<221> NAME/KEY: MISC_FEATURE
<222> LOCATION: (1)..(3)
<223> OTHER INFORMATION: MODIFIED WITH PHOSPHOROTHIOATE LINKAGE
<220> FEATURE:
<221> NAME/KEY: MISC_FEATURE
<222> LOCATION: (1)..(2)
<223> OTHER INFORMATION: MODIFIED WITH 2'-O-METHYLATION
<220> FEATURE:
<221> NAME/KEY: MISC_FEATURE
<222> LOCATION: (3)..(3)
<223> OTHER INFORMATION: MODIFIED WITH LOCKED NUCLEIC ACID MODIFICATION
<220> FEATURE:
<221> NAME/KEY: MISC_FEATURE
<222> LOCATION: (4)..(5)
<223> OTHER INFORMATION: MODIFIED WITH 2'-O-METHYLATION
<220> FEATURE:
<221> NAME/KEY: MISC_FEATURE
<222> LOCATION: (6)..(6)
<223> OTHER INFORMATION: MODIFIED WITH LOCKED NUCLEIC ACID MODIFICATION
<220> FEATURE:
<221> NAME/KEY: MISC_FEATURE
<222> LOCATION: (7)..(8)
<223> OTHER INFORMATION: MODIFIED WITH 2'-O-METHYLATION
<220> FEATURE:
<221> NAME/KEY: MISC_FEATURE
<222> LOCATION: (9)..(9)
<223> OTHER INFORMATION: MODIFIED WITH LOCKED NUCLEIC ACID MODIFICATION
<220> FEATURE:
<221> NAME/KEY: MISC_FEATURE
<222> LOCATION: (10)..(11)
<223> OTHER INFORMATION: MODIFIED WITH 2'-O-METHYLATION
<220> FEATURE:
<221> NAME/KEY: MISC_FEATURE
<222> LOCATION: (12)..(12)
<223> OTHER INFORMATION: MODIFIED WITH LOCKED NUCLEIC ACID MODIFICATION
<220> FEATURE:
<221> NAME/KEY: MISC_FEATURE
<222> LOCATION: (13)..(14)
<223> OTHER INFORMATION: MODIFIED WITH 2'-O-METHYLATION
<220> FEATURE:
<221> NAME/KEY: MISC_FEATURE
```

```
<222> LOCATION: (15)..(15)
<223> OTHER INFORMATION: MODIFIED WITH LOCKED NUCLEIC ACID MODIFICATION
<220> FEATURE:
<221> NAME/KEY: MISC_FEATURE
<222> LOCATION: (16)..(17)
<223> OTHER INFORMATION: MODIFIED WITH 2'-O-METHYLATION
<220> FEATURE:
<221> NAME/KEY: MISC_FEATURE
<222> LOCATION: (18)..(18)
<223> OTHER INFORMATION: MODIFIED WITH LOCKED NUCLEIC ACID MODIFICATION
<220> FEATURE:
<221> NAME/KEY: MISC_FEATURE
<222> LOCATION: (19)..(20)
<223> OTHER INFORMATION: MODIFIED WITH 2'-O-METHYLATION
<220> FEATURE:
<221> NAME/KEY: MISC_FEATURE
<222> LOCATION: (20)..(22)
<223> OTHER INFORMATION: MODIFIED WITH PHOSPHOROTHIOATE LINKAGE
<220> FEATURE:
<221> NAME/KEY: MISC_FEATURE
<222> LOCATION: (21)..(21)
<223> OTHER INFORMATION: MODIFIED WITH LOCKED NUCLEIC ACID MODIFICATION
<220> FEATURE:
<221> NAME/KEY: MISC_FEATURE
<222> LOCATION: (22)..(23)
<223> OTHER INFORMATION: MODIFIED WITH 2'-O-METHYLATION

<400> SEQUENCE: 11
ggcaatccaa cggaccutca ccu                                             23

<210> SEQ ID NO 12
<211> LENGTH: 23
<212> TYPE: DNA
<213> ORGANISM: ARTIFICIAL SEQUENCE
<220> FEATURE:
<223> OTHER INFORMATION: AMO_138_23_2 OR ANTI-MIR138-2
<220> FEATURE:
<221> NAME/KEY: MISC_FEATURE
<222> LOCATION: (1)..(3)
<223> OTHER INFORMATION: MODIFIED WITH PHOSPHOROTHIOATE LINKAGE
<220> FEATURE:
<221> NAME/KEY: MISC_FEATURE
<222> LOCATION: (1)..(2)
<223> OTHER INFORMATION: MODIFIED WITH 2'-O-METHYLATION
<220> FEATURE:
<221> NAME/KEY: MISC_FEATURE
<222> LOCATION: (3)..(3)
<223> OTHER INFORMATION: MODIFIED WITH LOCKED NUCLEIC ACID MODIFICATION
<220> FEATURE:
<221> NAME/KEY: MISC_FEATURE
<222> LOCATION: (4)..(5)
<223> OTHER INFORMATION: MODIFIED WITH 2'-O-METHYLATION
<220> FEATURE:
<221> NAME/KEY: MISC_FEATURE
<222> LOCATION: (6)..(6)
<223> OTHER INFORMATION: MODIFIED WITH LOCKED NUCLEIC ACID MODIFICATION
<220> FEATURE:
<221> NAME/KEY: MISC_FEATURE
<222> LOCATION: (7)..(8)
<223> OTHER INFORMATION: MODIFIED WITH 2'-O-METHYLATION
<220> FEATURE:
<221> NAME/KEY: MISC_FEATURE
<222> LOCATION: (9)..(9)
<223> OTHER INFORMATION: MODIFIED WITH LOCKED NUCLEIC ACID MODIFICATION
<220> FEATURE:
<221> NAME/KEY: MISC_FEATURE
<222> LOCATION: (10)..(11)
<223> OTHER INFORMATION: MODIFIED WITH 2'-O-METHYLATION
<220> FEATURE:
<221> NAME/KEY: MISC_FEATURE
<222> LOCATION: (12)..(12)
<223> OTHER INFORMATION: MODIFIED WITH LOCKED NUCLEIC ACID MODIFICATION
<220> FEATURE:
<221> NAME/KEY: MISC_FEATURE
<222> LOCATION: (13)..(14)
<223> OTHER INFORMATION: MODIFIED WITH 2'-O-METHYLATION
<220> FEATURE:
```

-continued

```
<221> NAME/KEY: MISC_FEATURE
<222> LOCATION: (15)..(15)
<223> OTHER INFORMATION: MODIFIED WITH LOCKED NUCLEIC ACID MODIFICATION
<220> FEATURE:
<221> NAME/KEY: MISC_FEATURE
<222> LOCATION: (16)..(17)
<223> OTHER INFORMATION: MODIFIED WITH 2'-O-METHYLATION
<220> FEATURE:
<221> NAME/KEY: MISC_FEATURE
<222> LOCATION: (18)..(18)
<223> OTHER INFORMATION: MODIFIED WITH LOCKED NUCLEIC ACID MODIFICATION
<220> FEATURE:
<221> NAME/KEY: MISC_FEATURE
<222> LOCATION: (19)..(20)
<223> OTHER INFORMATION: MODIFIED WITH 2'-O-METHYLATION
<220> FEATURE:
<221> NAME/KEY: MISC_FEATURE
<222> LOCATION: (20)..(22)
<223> OTHER INFORMATION: MODIFIED WITH PHOSPHOROTHIOATE LINKAGE
<220> FEATURE:
<221> NAME/KEY: MISC_FEATURE
<222> LOCATION: (21)..(21)
<223> OTHER INFORMATION: MODIFIED WITH LOCKED NUCLEIC ACID MODIFICATION
<220> FEATURE:
<221> NAME/KEY: MISC_FEATURE
<222> LOCATION: (22)..(23)
<223> OTHER INFORMATION: MODIFIED WITH 2'-O-METHYLATION

<400> SEQUENCE: 12
cggcctgatu cacaacacca gcu                                              23

<210> SEQ ID NO 13
<211> LENGTH: 23
<212> TYPE: DNA
<213> ORGANISM: ARTIFICIAL SEQUENCE
<220> FEATURE:
<223> OTHER INFORMATION: AMO_138_23_3 OR ANTI-MIR138-3
<220> FEATURE:
<221> NAME/KEY: MISC_FEATURE
<222> LOCATION: (1)..(3)
<223> OTHER INFORMATION: MODIFIED WITH PHOSPHOROTHIOATE LINKAGE
<220> FEATURE:
<221> NAME/KEY: MISC_FEATURE
<222> LOCATION: (1)..(2)
<223> OTHER INFORMATION: MODIFIED WITH 2'-O-METHYLATION
<220> FEATURE:
<221> NAME/KEY: MISC_FEATURE
<222> LOCATION: (3)..(3)
<223> OTHER INFORMATION: MODIFIED WITH LOCKED NUCLEIC ACID MODIFICATION
<220> FEATURE:
<221> NAME/KEY: MISC_FEATURE
<222> LOCATION: (4)..(4)
<223> OTHER INFORMATION: MODIFIED WITH 2'-O-METHYLATION
<220> FEATURE:
<221> NAME/KEY: MISC_FEATURE
<222> LOCATION: (5)..(5)
<223> OTHER INFORMATION: MODIFIED WITH LOCKED NUCLEIC ACID MODIFICATION
<220> FEATURE:
<221> NAME/KEY: MISC_FEATURE
<222> LOCATION: (6)..(7)
<223> OTHER INFORMATION: MODIFIED WITH 2'-O-METHYLATION
<220> FEATURE:
<221> NAME/KEY: MISC_FEATURE
<222> LOCATION: (8)..(8)
<223> OTHER INFORMATION: MODIFIED WITH LOCKED NUCLEIC ACID MODIFICATION
<220> FEATURE:
<221> NAME/KEY: MISC_FEATURE
<222> LOCATION: (9)..(9)
<223> OTHER INFORMATION: MODIFIED WITH 2'-O-METHYLATION
<220> FEATURE:
<221> NAME/KEY: MISC_FEATURE
<222> LOCATION: (10)..(10)
<223> OTHER INFORMATION: MODIFIED WITH LOCKED NUCLEIC ACID MODIFICATION
<220> FEATURE:
<221> NAME/KEY: MISC_FEATURE
<222> LOCATION: (11)..(11)
<223> OTHER INFORMATION: MODIFIED WITH 2'-O-METHYLATION
```

```
<220> FEATURE:
<221> NAME/KEY: MISC_FEATURE
<222> LOCATION: (12)..(12)
<223> OTHER INFORMATION: MODIFIED WITH LOCKED NUCLEIC ACID MODIFICATION
<220> FEATURE:
<221> NAME/KEY: MISC_FEATURE
<222> LOCATION: (13)..(14)
<223> OTHER INFORMATION: MODIFIED WITH 2'-O-METHYLATION
<220> FEATURE:
<221> NAME/KEY: MISC_FEATURE
<222> LOCATION: (15)..(15)
<223> OTHER INFORMATION: MODIFIED WITH LOCKED NUCLEIC ACID MODIFICATION
<220> FEATURE:
<221> NAME/KEY: MISC_FEATURE
<222> LOCATION: (16)..(16)
<223> OTHER INFORMATION: MODIFIED WITH 2'-O-METHYLATION
<220> FEATURE:
<221> NAME/KEY: MISC_FEATURE
<222> LOCATION: (17)..(17)
<223> OTHER INFORMATION: MODIFIED WITH LOCKED NUCLEIC ACID MODIFICATION
<220> FEATURE:
<221> NAME/KEY: MISC_FEATURE
<222> LOCATION: (18)..(18)
<223> OTHER INFORMATION: MODIFIED WITH 2'-O-METHYLATION
<220> FEATURE:
<221> NAME/KEY: MISC_FEATURE
<222> LOCATION: (19)..(19)
<223> OTHER INFORMATION: MODIFIED WITH LOCKED NUCLEIC ACID MODIFICATION
<220> FEATURE:
<221> NAME/KEY: MISC_FEATURE
<222> LOCATION: (20)..(22)
<223> OTHER INFORMATION: MODIFIED WITH PHOSPHOROTHIOATE LINKAGE
<220> FEATURE:
<221> NAME/KEY: MISC_FEATURE
<222> LOCATION: (20)..(20)
<223> OTHER INFORMATION: MODIFIED WITH 2'-O-METHYLATION
<220> FEATURE:
<221> NAME/KEY: MISC_FEATURE
<222> LOCATION: (21)..(21)
<223> OTHER INFORMATION: MODIFIED WITH LOCKED NUCLEIC ACID MODIFICATION
<220> FEATURE:
<221> NAME/KEY: MISC_FEATURE
<222> LOCATION: (22)..(23)
<223> OTHER INFORMATION: MODIFIED WITH 2'-O-METHYLATION

<400> SEQUENCE: 13
cggccugaut cacaacacca gcu                                          23
```

MODIFIED ANTIMIR-138 OLIGONUCLEOTIDES

CROSS-REFERENCE TO RELATED APPLICATIONS

This patent application is a U.S. National Phase Application under 35 U.S.C. § 371 of International Application No. PCT/SG2015/050245, filed 31 Jul. 2015, entitled MODIFIED ANTIMIR-138 OLIGONUCLEOTIDES, which claims the benefit of priority of Singapore Patent Application No. 10201404535S, filed 31 Jul. 2014, the contents of which were incorporated by reference in their entirety for all purposes.

INCORPORATION BY REFERENCE

This patent application incorporates by reference the material (i.e., Sequence Listing) in the ASCII text file named Sequence_Listing.txt, created on Jan. 3, 2017, having a file size of 15,112 bytes.

FIELD OF THE INVENTION

The present invention relates to biochemistry in particular biomarkers. In particular, the present invention relates to oligonucleotides that can regulate the expression of biomarker miR-138, pharmaceutical compositions and methods of using the biomarkers thereof.

BACKGROUND OF THE INVENTION

MicroRNAs (miRNAs) are endogenous small noncoding RNAs that regulate various physiological pathways such as cellular differentiation and proliferation via gene silencing. The microRNAs are thought to contribute to the initiation, progression and eventual metastasis of various proliferative diseases. For example, dysregulation of the expression of a miRNA may lead to aberrant expression of its target proteins, resulting in an altered phenotype in a cell. Impaired miRNA regulatory network is known to be one of the key mechanisms in the pathogenesis of proliferative diseases such as cancer. Thus, there is a need to provide molecules that have the potential to influence the expression of miRNA.

SUMMARY OF THE INVENTION

In one aspect, there is provided an oligonucleotide comprising at least one locked nucleic acid (LNA), wherein the oligonucleotide is substantially complementary to a nucleotide sequence of miR-138, and wherein the oligonucleotide reduces or inhibits the activity of one or more miR-138.

In another aspect, there is provided a pharmaceutical composition comprising an effective amount of the oligonucleotide as described herein, or a pharmaceutically-acceptable salt thereof, and a pharmaceutically-acceptable carrier or diluent.

In another aspect, there is provided a method of treating a proliferative disease in a subject in need thereof comprising administering the oligonucleotide as described herein to the subject.

In another aspect, there is provided a use of an oligonucleotide as described herein in the manufacture of a medicament for treating proliferative disease in a subject in need thereof.

In another aspect, there is provided a method of reducing or inhibiting the activity of miR-138 in a cell comprising contacting the cell with the oligonucleotide as described herein.

BRIEF DESCRIPTION OF THE DRAWINGS

The invention will be better understood with reference to the detailed description when considered in conjunction with the non-limiting examples and the accompanying drawings, in which:

FIG. 1 shows day 7 post-transfection with 40 nanomoles of anti-sense oligos anti-miR-138-1 (SEQ ID NO: 10), anti-miR-138-2 (SEQ ID NO: 12), anti-miR-138-3 (SEQ ID NO: 13), anti-miR-138-4 (SEQ ID NO; 7 or "Oligo-4") and negative controls ("scrambled control" for anti-miR-138-1, anti-miR-138-2, and anti-miR-138-3; "control sequence" for Oligo-4) of U87MG cells. Sequences of anti-sense oligos used in FIG. 1 are provided in Table 1 below. FIG. 1 shows that whilst anti-miR-138 oligonucleotides inhibit the growth of U87MG cells, control anti-sense oligos were not found to inhibit the proliferation of U87MG cells. Thus, showing anti-miR-138 oligonucleotide can prevent the proliferation of malignant gliomas.

FIG. 2 shows modified anti-miR138-3 (i.e. AMO_138_23_3 in Table 1) oligonucleotides are as effective as miR-138 lentiviral antagomir in inhibiting the expression of miR-138.

FIG. 3 shows that, as compared to two non-targeting controls (i.e. scrambled and anti-miR-106), anti-miR-138-3 (i.e. AMO_138_23_3 in Table 1) oligonucleotides significantly down-regulates the expression of miR-138. **p<0.001.

FIG. 4 shows transfection with modified oligonucleotides anti-miR-138-1 (SEQ ID NO: 10), anti-miR-138-2 (SEQ ID NO: 12), anti-miR-138-3 (SEQ ID NO: 13), anti-miR-138-4 (SEQ ID NO; 7 or "Oligo-4") and negative controls ("scrambled control" for anti-miR-138-1, anti-miR-138-2, and anti-miR-138-3; "control sequence" for Oligo-4). Thus, FIG. 4 shows the oligonucleotides as described in the Example section are capable of down-regulating the expression of miR-138 in human glioblastoma cells.

FIG. 5 shows that, as compared to other oligonucleotides used, anti-miR-138-3 and anti-miR-138-4 oligonucleotides appear to up-regulate more TXNIP.

FIG. 6 shows that anti-miR138-3 and anti-miR138-4 oligonucleotides appear to up-regulate PANX2 gene better.

FIG. 7 shows that anti-miR138-2, anti-miR138-3 and anti-miR138-4 oligonucleotides appear to up-regulate CASP3 better than anti-miR138-1.

FIG. 8 shows that both anti-miR138-3 and anti-miR138-4 oligonucleotides appear to up-regulate MXD1 gene more than anti-miR138-1 and anti-miR138-2.

FIG. 9 shows a trend of better performance of cMYC regulation with anti-miR138-3 oligonucleotide.

FIG. 10 shows a trend of better performance of GAAD45A regulation with anti-miR138-3 and anti-miR138-4 oligonucleotides.

FIG. 11 shows a trend of better performance of AURKA regulation with anti-miR138-2 and anti-miR138-3 oligonucleotides.

FIG. 12 shows a trend of better performance of BLCAP regulation with anti-miR138-1, anti-miR138-3 and anti-miR138-4 oligonucleotides.

FIG. 13 shows a trend of better performance of BCL2 regulation with anti-miR138-3 and anti-miR138-4 oligonucleotides.

FIG. 14 shows a trend of better performance of HIF1A regulation with anti-miR138-1, anti-miR138-2 and anti-miR138-3 oligonucleotides.

FIG. 15 shows a trend of better performance of LASP1 regulation with anti-miR138-1, and anti-miR138-3 oligonucleotides.

FIG. 16** shows anti-miR-138-3 oligonucleotide up-regulates or down-regulates miR-138 target level.

FIG. 17 shows U87MG cells proliferate to confluence density when transfected with either scrambled or anti-miR-106a oligonucleotides (left-most column and middle column). In contrast, cells transfected with anti-miR-138 (far-right column) did not appear to have proliferated and a lot of apoptotic blebs or cell debris is observed. Thus, FIG. 17 shows anti-miR-138-3 oligonucleotides block proliferation and lead to apoptotic death of U87MG cells.

FIG. 18 shows U87MG cells transfected with anti-miR-138-3 oligonucleotide fail to form intracranial tumors. By day 26, no luciferase positive cells were detected in mice injected with U87MG transformed with anti-miR-138-3 oligonucleotides. In contrast, U87MG cells transfected with control anti-miR grew linearly from day 10 to day 26 post-injection. Thus, FIG. 18 shows transfection of anti-miR138 can inhibit the growth of glioma cells in vivo.

FIG. 19 shows a bar graph of level of miR-138 after transfection with AMO_138_11_Cap_PS (i.e. modified oligonucleotide with complete locked nucleic acid modification and phosphorothioate (PS) modification at either ends of the oligonucleotide, third row of Table 1) or its control (i.e. AMO_Control_11_PS ends, fourth row of Table 1). Knock down of miR-138 in cell line was observed, no significant toxic cell death observed. Forty nanomoles of oligonucleotides were used in all experiments. Thus, FIG. 19 shows modified anti-miR-138 oligonucleotides of 11 nucleotides can knock down miR-138 in cell lines.

FIG. 20 shows modified anti-miR-138 oligonucleotides of 23 nucleotides (mer) can knock down miR-138 in cell lines and cause apoptotic cell death.

FIG. 21 shows depletion of miR-138 leads the inhibition of cell proliferation.

FIG. 23 shows anti-miR-138-3 oligonucleotide up-regulates or down-regulates miR-138 target level.

FIG. 25 shows miR-138 expression in breast cancer can be regulated using anti-miR-138.

FIG. 26 shows depletion of miR-138 in breast cancer cell line leads to a decrease in S-phase cells and an increase in Sub-G1 and G2/M phase cells, demonstrating depletion of miR-138 in breast cancer cell line leads to senescence.

BRIEF DESCRIPTION OF THE TABLES

Figure 1:
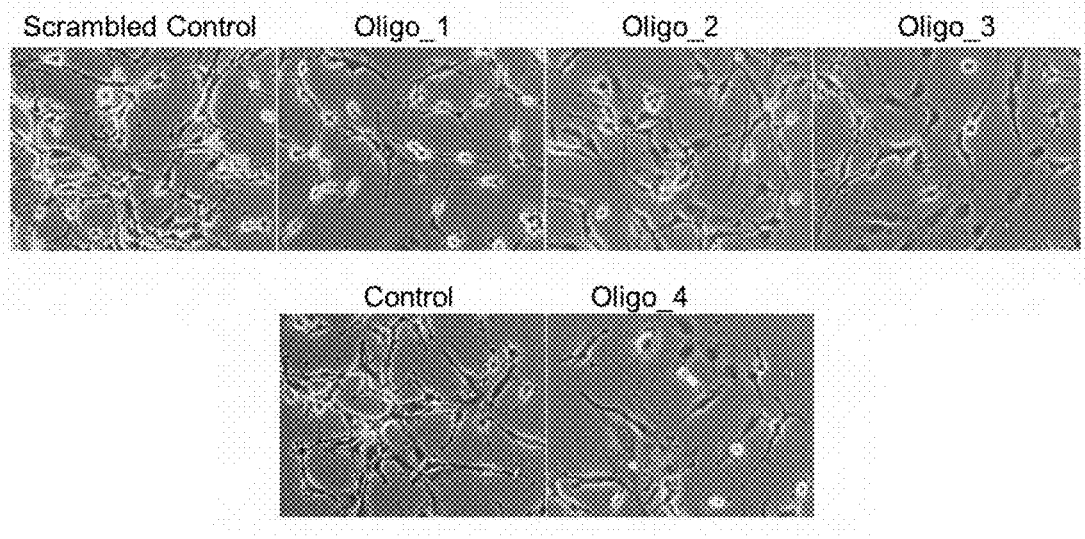
FIG. 1 shows light microscopic images of the U87MG cells (human glioblastoma cell line) transfected with anti-miR-138 oligonucleotides as described in the Example section. In particular.

The invention will be better understood with reference to the detailed description when considered in conjunction with the non-limiting examples and the accompanying Table, in which:

Table 1 lists exemplary modified anti-miR138, their knockdown efficiency and the cell phenotype after treatment with the modified anti-miR138 oligonucleotides.

DETAILED DESCRIPTION OF THE PRESENT INVENTION

MicroRNAs (miRNAs) have long been considered to be important post-transcriptional regulators of gene expression in many developmental and cellular processes. Some miRNAs have also been linked to the initiation and progression of proliferative diseases, such as cancer. Thus, molecules that are able to regulate miRNA expression would be advantageous to the regulation of certain diseases like proliferative diseases.

One example of miRNAs that is known to play a role in diseases is the miR-138. For example, high expression of miR-138 has been found to be associated with poor prognosis for survival of subjects having proliferative diseases. Hence, it is envisaged that a molecule that is capable of regulating the expression of miR138 would proof to be useful. Thus, there is a need to provide an oligonucleotide that reduces or inhibits the activity of one or more miR-138.

Thus, in one example, there is provided an oligonucleotide that is capable of reducing or inhibiting the activity of one or more miR-138 (such as matured miR-138 or pre-miR-138). In one example, the oligonucleotide comprises at least one locked nucleic acid (LNA) and wherein the oligonucleotide is substantially complementary to a nucleotide sequence of miR-138. Thus, in one example, there is provided an oligonucleotide comprising at least one locked nucleic acid (LNA), wherein the oligonucleotide is substantially complementary to a nucleotide sequence of miR-138, and wherein the oligonucleotide reduces or inhibits the activity of one or more miR-138.

As used herein, the term "complementary" refers to an amount of base pairing between oligonucleotide strands. In one example, the amount of complementarity between two oligonucleotides can be expressed in percentages. For example, a first oligonucleotide strand is fully complementary (i.e. 100% complementary) to a second nucleotide strand if base pairing is formed between each contiguous nucleotide along the first and second oligonucleotide strands. In one example, the full length or a portion of the length of an oligonucleotide strand may be complementary (e.g. fully complementary) to another oligonucleotide strand. Complementary oligonucleotide strands can be a different length or the same length.

As used herein, the term "substantially", when used in conjunction with the term "complementary", refers to almost complete or nearly complete base pairing of two oligonucleotides. For example, a first oligonucleotide that is "substantially" complementary to a second oligonucleotide would mean that the first oligonucleotide is either completely complementary of the second oligonucleotide, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99% complementary to the second oligonucleotide. In one example, a substantially complementary oligonucleotide may have one, or two, or three mismatched base pairing. It is contemplated that the oligonucleotide as described herein are sufficiently complementary when the amount of complementarity is sufficient to inhibit the biological activity of miR-138.

As used herein, the term "microRNA" or "miRNA" refers to short, non-coding RNAs derived from endogenous genes that act as post-transcriptional regulators of gene expression. The term "microRNA-138" or "miRNA-138" or "miR-138" refers to an RNA oligonucleotide consisting of 23 nucleotides in length, which has been found to have a biological role in human diseases, such as proliferative diseases. The miR-138 exerts its effect on its target by regulating various genes known to play a role in proliferation or apoptosis.

Hence, the effect of miR-138 on various genes is described in the present disclosure as the "activity of miR-138". Therefore, as used herein, the term "activity" of miR-138 relates to the regulations of genes that are directly or indirectly affected by the change in the expression level of miR-138. For example, the activity of miR-138 relates to the regulation of genes, including but not limited to, MAX dimerization protein 1 (MXD1) gene, caspase 3 gene (CASP3), bladder cancer associated protein gene (BLCAP), thioredoxin interacting protein gene (TXNIP), tumor suppressor candidate 2 gene (TUSC2), pannexin 2 gene (PANX2), growth arrest and DNA damage-inducible gene 45 alpha gene (GADD45α), hypoxia inducible factor 1 alpha gene (HIF1α), v-myc avian myelocytomatosis viral oncogene homolog gene (cMYC), B-cell CLL/lymphoma 2 gene (BCL2), LIM and SH3 domain protein 1 gene (LASP1), aurora kinase A gene (AURKA) and the like. In one example, the sequence of a matured miR-138 is AGCTGGTGTTGTGAATCAGGCCG (SEQ ID NO: 1).

As used herein, the term "reduces" or "inhibits", when used in relation with the activity of miR-138, refers to the decrease or the reduction of or lessening of the effect of miR138 in a cell or a subject. For example, the reduction or inhibition relates to the lessening or down-regulation of the expression of certain genes associated with diseases such as proliferative diseases. The lessening, inhibition or reduction of the activity or effect of miR-138 may be provided in a cell or a subject by the upregulation or downregulation of genes that are regulated by miR-138. Thus, in one example, the oligonucleotides as described herein may be capable of up-regulating the expression of genes including, but not limited to, MAX dimerization protein 1 (MXD1) gene, caspase 3 gene (CASP3), bladder cancer associated protein gene (BLCAP), thioredoxin interacting protein gene (TXNIP), tumor suppressor candidate 2 gene (TUSC2), pannexin 2 gene (PANX2) and/or growth arrest and DNA damage-inducible gene 45 alpha gene (GADD45α). In one example, the oligonucleotides as described herein may be capable of down-regulating the expression of genes including, but not limited to, hypoxia inducible factor 1 alpha gene (HIF1α), v-myc avian myelocytomatosis viral oncogene homolog gene (cMYC), B-cell CLL/lymphoma 2 gene (BCL2), LIM and SH3 domain protein 1 (LASP1) and/or aurora kinase A gene (AURKA).

As used herein, the terms "polynucleotide", "nucleic acid", or "oligonucleotide" refers to a linear polymer of nucleosides (including deoxyribonucleosides, ribonucleosides, or analogs thereof) joined by inter-nucleosidic linkages Whenever a polynucleotide such as an oligonucleotide is represented by a sequence of letters, such as "ATGC," it will be understood that the nucleosides are in 5'→3' order from left to right and that "A" denotes deoxyadenosine, "C" denotes deoxycytidine, "G" denotes deoxyguanosine, and "T" denotes deoxythymidine, unless otherwise noted. The letters A, C, G, and T can be used to refer to the bases themselves, to nucleosides, or to nucleotides comprising the bases, as is standard in the art. This term includes oligonucleotides composed of naturally occurring nucleobases, sugars and internucleoside (backbone) linkages as well as oligonucleotides having non-naturally-occurring portions which function similarly or with specific improved functions. In naturally occurring polynucleotides, the internucleoside linkage is typically a phosphodiester bond, and the subunits are referred to as "nucleotides." The term "oligonucleotide" may also include fully or partly modified or substituted oligonucleotides, such as in the bases and/or sugars.

In one example, the oligonucleotide as described herein may be an anti-miRNA oligonucleotide. As used herein, the term "anti-miR-138 oligonucleotide" or "anti-miRNA-138 oligonucleotide" refers to oligonucleotides that are substantially complementary to, or essentially complementary to (i.e. may comprise one or two mismatches), to the miR-138, or analogue thereof or corresponding subsequences thereof. In one example, the anti-miR-138 may comprise a contiguous nucleotide sequence which is complementary or essentially complementary to the entire mature miR-138 (i.e. SEQ ID NO: 1) or to the seed sequence of miR138, or the anti-miR-138 may comprise a contiguous nucleotide sequence which is complementary or essentially complementary to a subsequence of the mature microRNA or pre-microRNA-such sub-sequence (and therefore the corresponding contiguous nucleotide sequence). In one example, the anti-miR-138 may comprise a contiguous nucleotide sequence that is complementary or essentially complementary to the seed sequence of the miR-138.

As used herein, the term "seed sequence" refers to the sequence that may have a role in the binding of the miRNA to the mRNA. In general, the seed sequence or seed region may be a conserved heptametrical sequence that is mostly situated at positions 2-7 from the miRNA 5'-end. Even though base pairing of miRNA and its target mRNA does not match perfect, the "seed sequence" may be perfectly complementary.

In one example, the anti-miR-138 oligonucleotide as described herein may be 11 nucleotides in length, such as between 8 to 26 nucleotides, such as 11, 12, 13, 14, 15, 16, 17, 18, 19, 20, 21, 22, 23, 24, 25, 26 nucleotides in length, such as between 11 to 16, 17 to 20 or 21 to 23 nucleotides in length. In one example, the oligonucleotide as described herein may have between 8 to 27 nucleotides. In one example, the oligonucleotide may have between 11 to 23 nucleotides in length, or from between 15 to 23 nucleotides in length, or from between 17 to 23 nucleotides in length, or 8 nucleotides in length, or 9 nucleotides in length, or 10 nucleotides in length, or 11 nucleotides in length, or 12 nucleotides in length, or 13 nucleotides in length, or 14 nucleotides in length, or 15 nucleotides in length, or 16 nucleotides in length, or 17 nucleotides in length, or 18 nucleotides in length, or 19 nucleotides in length, or 20 nucleotides in length, or 21 nucleotides in length, or 22 nucleotides in length, or 23 nucleotides in length, or 24 nucleotides in length, or 25 nucleotides in length, or 26 nucleotides in length. In one example, the oligonucleotide as described herein may comprise or consist of the sequence such as, but is not limited to, 5'-ACAACACCAGC-3' (SEQ ID NO: 4; seed sequence of antimiR-138), 5'-CGGC-CUGAUTCACAACACCAGCU-3' (SEQ ID NO: 2; antim-RNA-138) and 5'-CGGCCUGAUUCACAACACCAGCU-3' (SEQ ID NO: 3; antimRNA-138).

As used herein, the term "locked nucleic acid" refers to a modification of RNA nucleotide that renders the RNA to be an inaccessible RNA. Thus, in one example, "locked nucleic acid" refers to an inaccessible RNA, where a locked nucleic acid (LNA) nucleotide is modified with an extra bridge connecting the 2' oxygen and 4' carbon. LNA is a modification of RNA that contains an oxy-methylene bridge between the 2' and 4' carbons in the ribose ring. This bridge creates a bi-cyclic structure that locks the conformation of the ribose. Thus, in one example, the locked nucleic acid creates a bi-cylic structure that locks the conformation of the ribose. The bi-cyclic structure may be created by ribose moiety modification, which creates a bridge connecting 2' oxygen to 4' carbon. In one example, the bridge that connects the 2' oxygen to 4' carbon may be an ethylene, methylene or oxy-methylene bridge. Without wishing to be bound by theory, it is believe that the bi-cyclic structure of the locked nucleic acid modification that locks the conformation of the ribose in RNA is key to the high stability and affinity of locked nucleic acid to its complementary nucleotide sequence.

The inventor of the present disclosure finds that specific nucleotide modification provides for an anti-miR138 that surprisingly works better than full sequence modification. Thus, in one example, the oligonucleotide may contain at least one, or at least two, or at least three, or at least four, or at least five, or at least six, or at least seven, or at least eight, or at least nine, or at least ten, or at least 11, or at least 12, or at least 13, or at least 14, or at least 15, or at least 16, or at least 17, or at least 18, or at least 19, or at last 20, or at least 21, or at least 22, or at least 23 or at least 24, or at least 25, or at least 26, or more locked nucleic acid(s). In one example, the locked nucleic acid modification may be present in half of the nucleic acids of the oligonucleotide. In one example, the locked nucleic acid modification may be present in 20-100% of the nucleic acids of the oligonucleotide as described herein. In one example, the locked nucleic acids may be in all of the nucleic acid of the oligonucleotide as described herein. In one example, the oligonucleotide may contain at least 5 to 12 locked nucleic acids. In one example, the oligonucleotide may contain at least 10 to 12 locked nucleic acids. In one example, the oligonucleotide may contain 6 to 11 locked nucleic acids. In one example, all of the nucleotide of the oligonucleotide as described herein may be locked nucleic acid modified. In one example, not all nucleotides of the oligonucleotide of the present disclosure are modified by the locked nucleic acid modification or locked-nucleic acid free nucleotide. Thus, in one example, the oligonucleotide as described herein may comprise at least one, or at least two, or at least three, or at least four, or at least five, or at least six, or at least seven, or at least eight, or at least nine, or at least ten, or at least 11, or at least 12, or at least 13, or at least 14, or at least 15, or at least 16, or at least 17, or at least 18, or at least 19, or at least 20 or at least 21 non-locked nucleic acid. In one example, the non-locked nucleic acid may be present in 0-80% of the nucleotides of the oligonucleotide as described herein. In one example, the oligonucleotide may contain about 11 to 18 non-locked nucleic acid modified nucleotides. In one example, the oligonucleotide may contain about 11 to 16 non-locked nucleic acid modified nucleotides. In one example, the non-locked nucleic acid may be comprised at least once, or at least two times, or at least three times, or at least four times, or at least five times, or at least six times, or at least seven times, or at least eight time, or at least nine times, or at least ten times, as 2 to 4, or 2 to 3, or 2 contiguous nucleic acid. Thus, in one example, the oligonucleotide as described herein may not contain a stretch of nucleic acid with more than one, or more than two, or more than three contiguous locked nucleic acids.

In one example, the locked nucleic acid modification may be present at any suitable positions as long as there are contiguous nucleic acids that are non-locked nucleic acids. Thus, in one example, the locked nucleic acid modification may be present at positions 1, 2, 3, 4, 5, 6, 7, 8, 9, 10, 11, 12, 13, 14, 15, 16, 17, 18, 19, 20, 21, or 22 of an oligonucleotide as described herein. In one example, the oligonucleotide as described herein may comprise or consist of the sequence 5'-ACAACACCAGC-3' (SEQ ID NO: 4; seed sequence of antimiR-138), 5'-CGGCCUGAUTCA-CAACACCAGCU-3' (SEQ ID NO: 2; antimRNA-138) and 5'-CGGCCUGAUUCACAACACCAGCU-3' (SEQ ID NO: 3; antimRNA-138), wherein the SEQ ID NO: 2 and SEQ ID NO:3, independently, may include at least one locked nucleic acid modification. In one example, the locked nucleic acid modification may be present at either SEQ ID NO: 2 or SEQ ID NO: 3. In one example, the locked nucleic acid modification may be present at positions 3, 5, 8, 10, 12, 15, 17, 19 and 21 of an anti-miR138, such as SEQ ID NO: 2, wherein position 1 of the SEQ ID NO: 2 is the 5' end terminus and position 23 of SEQ ID NO: 2 is the 3' end terminus.

Figure 2:
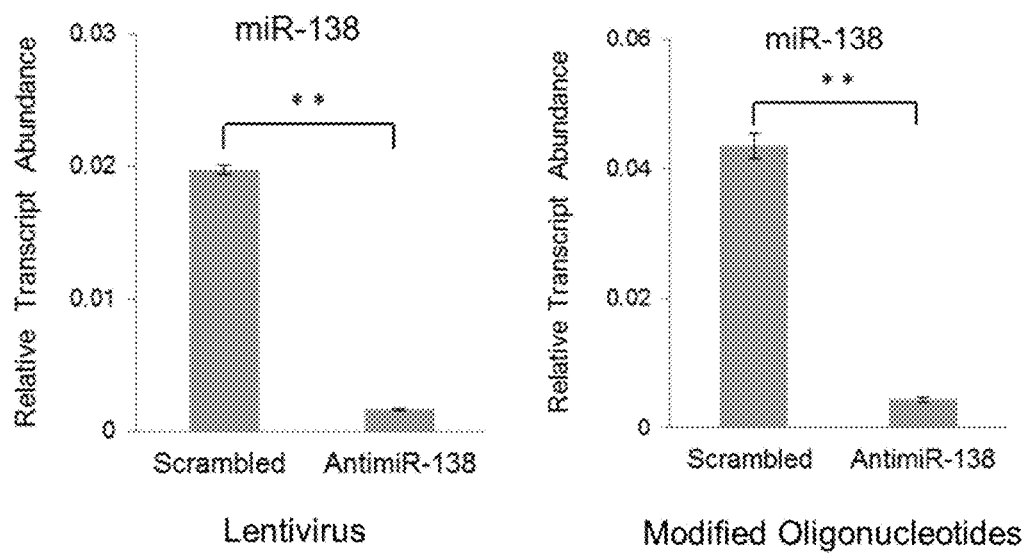
FIG. 2 shows bar graphs of the results of miRNA quantification of miR-138 levels in U87MG cells (human glioblastoma cell line). RNA was isolated from cells harvested 7 days after transfection with anti-miR-138 oligonucleotides described in FIG. 1. Left panel of FIG. 2 shows the regulation of miR-138 expression by lentiviral antagomir; Right panel of FIG. 2 shows modified anti-miR-138 oligonucleotides inhibit miR-138 expression in U87MG cells. Thus.
Figure 3:
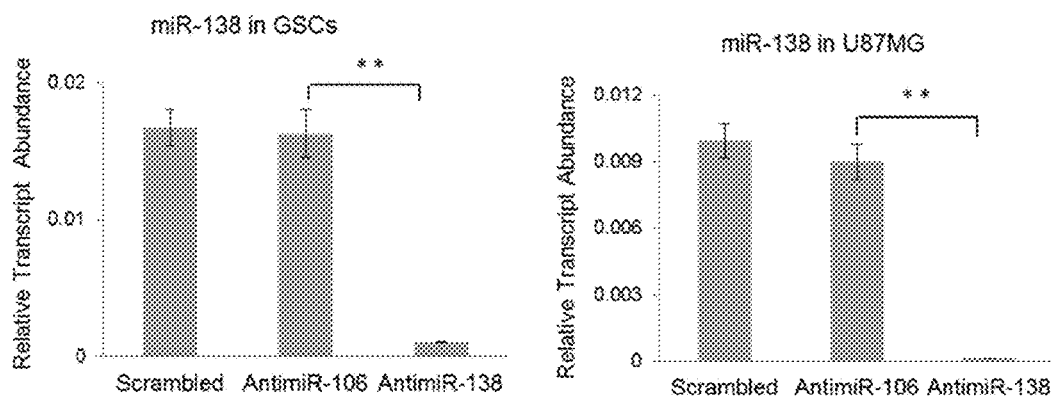
FIG. 3 shows regulation of miR-138 expression in both the glioblastoma stem cells (GSCs) and U87MG (human glioblastoma cell line). In particular.
Figure 4:
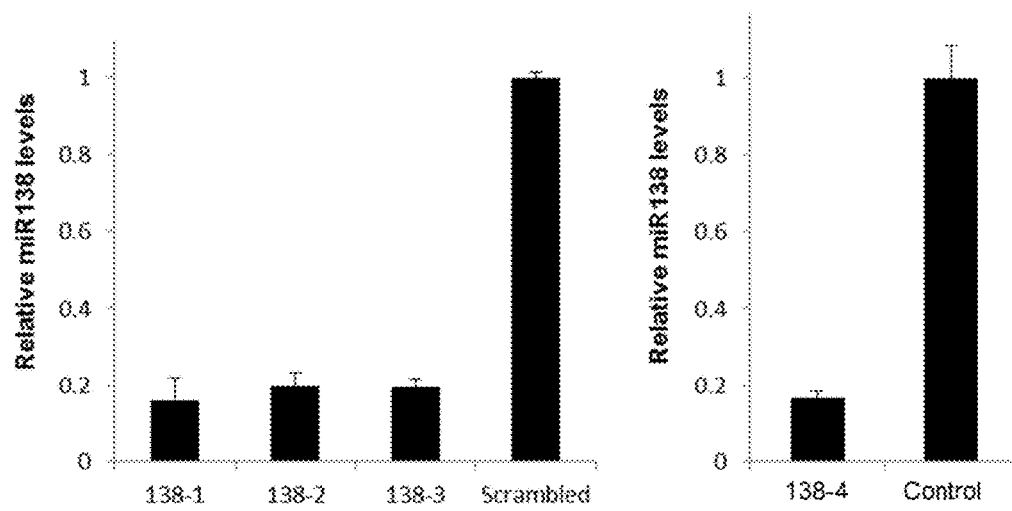
FIG. 4 shows the relative expression level of miR-138 in U87MG cells (human glioblastoma cell line) after transfection with anti-miR-138 oligonucleotides.
Figure 5:
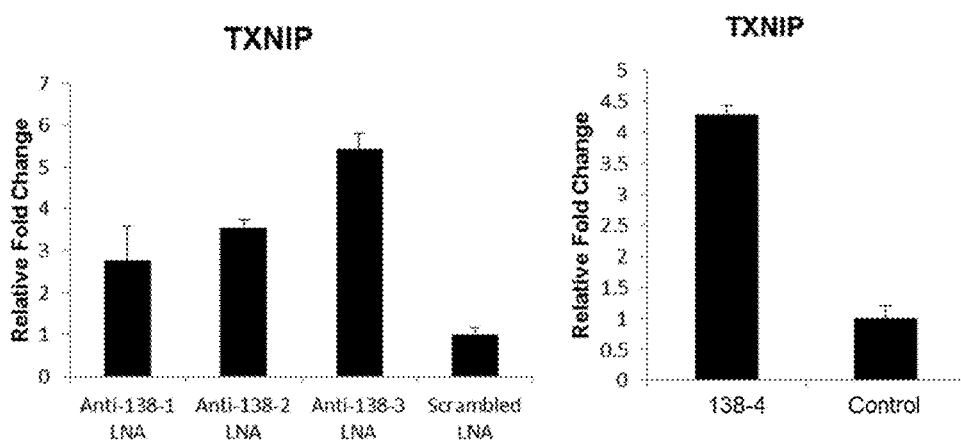
FIG. 5 shows the regulation of TXNIP gene (Thioredoxin-interacting protein gene) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13), and anti-miR-138-4 (SEQ ID NO; 7 or "Oligo-4" or "138-4") significantly up-regulates TXNIP gene.
Figure 6:
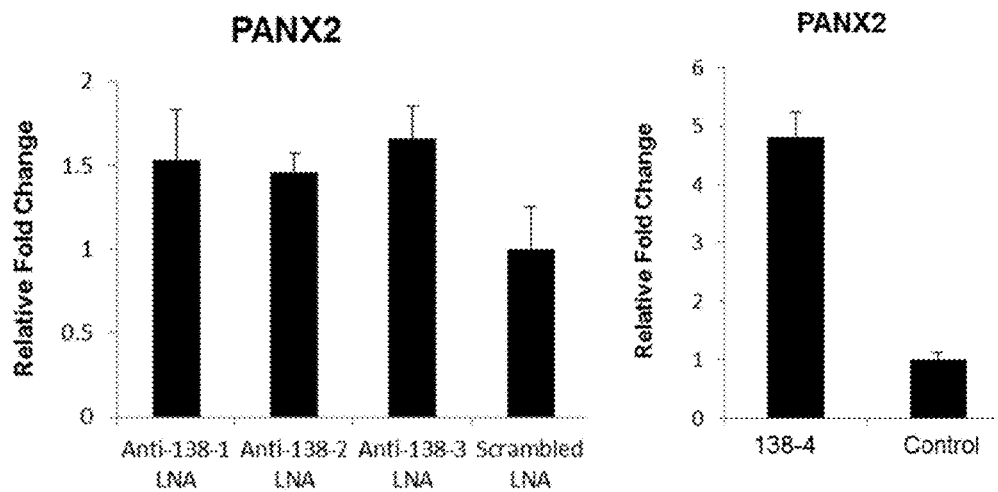
FIG. 6 shows the regulation of PANX2 gene (pannexin 2) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13) and anti-miR-138-4 (SEQ ID NO; 7 or "Oligo-4" or "138-4" or AMO_138_11_cap_PS) significantly up-regulates PANX2 gene.
Figure 7:
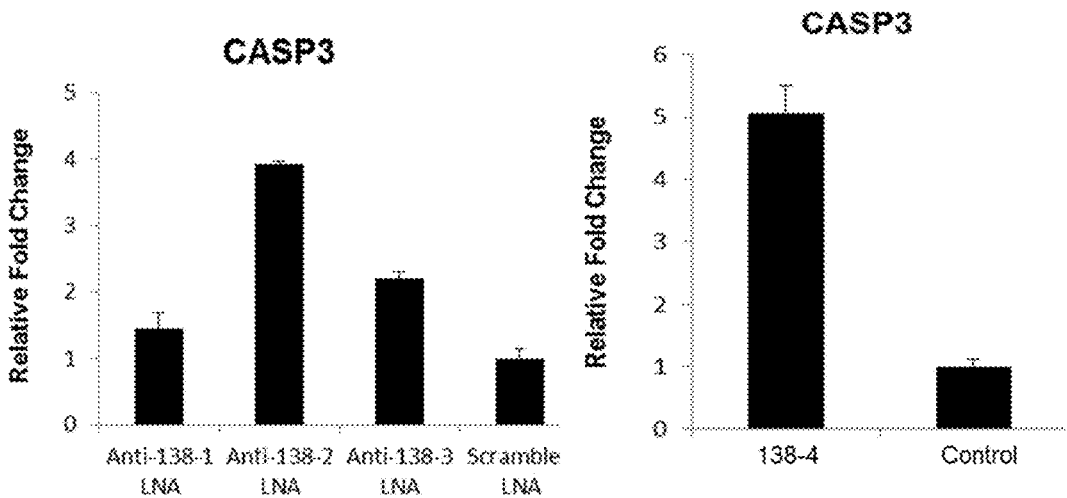
FIG. 7 shows the regulation of CASP3 gene (caspase-3) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13), and anti-miR-138-4 (SEQ ID NO; 7 or "Oligo-4" or "138-4" or AMO_138_11_cap_PS) significantly up-regulates CASP3 gene.
Figure 8:
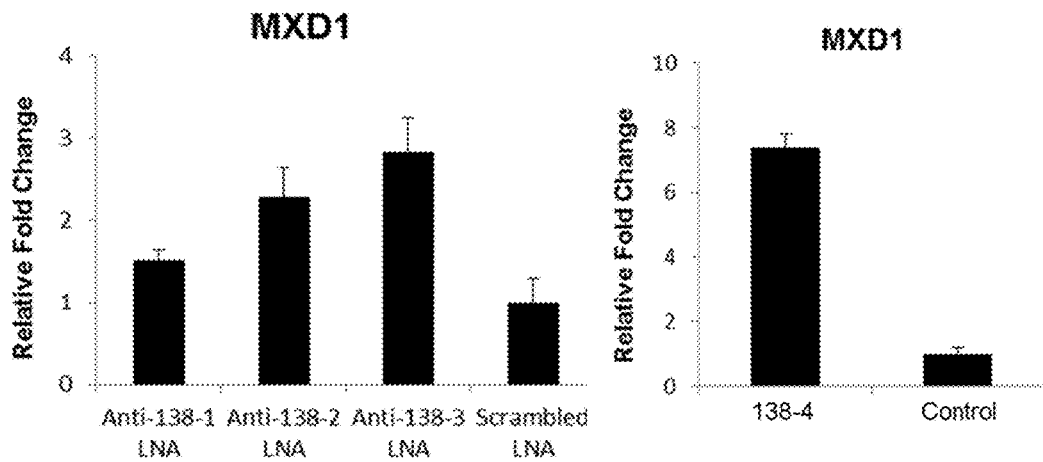
FIG. 8 shows the regulation of MXD1 gene (MAX dimerization protein 1) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13), and anti-miR-138-4 (SEQ ID NO; 7 or "Oligo-4" or "138-4" or AMO_138_11_cap_PS) significantly up-regulates MXD1 gene.
Figure 9:
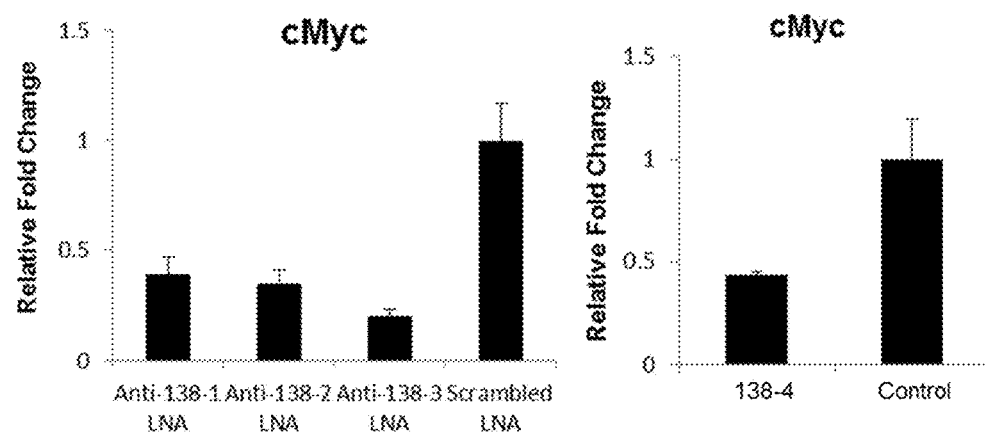
FIG. 9 shows the regulation of cMYC gene (v-myc avian myelocytomatosis viral oncogene homolog gene) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13), and anti-miR-138-4 (SEQ ID NO; 7 or "Oligo-4" or "138-4" or AMO_138_11_cap_PS) significantly down-regulates cMYC gene.
Figure 10:
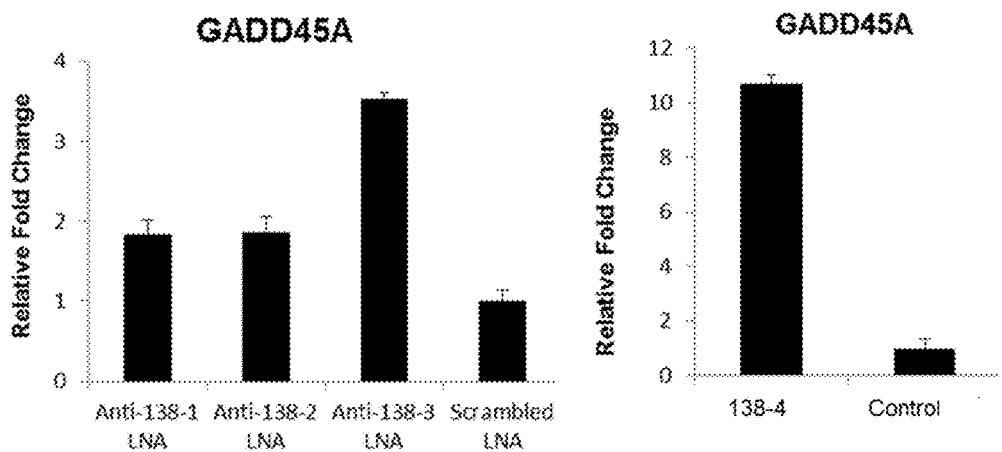
FIG. 10 shows the regulation of GAAD45A gene (DNA damage-inducible gene 45 alpha) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13), and anti-miR-138-4 (SEQ ID NO; 7 or "Oligo-4" or "138-4" or AMO_138_11_cap_PS) significantly up-regulates GAAD45A gene.
Figure 11:
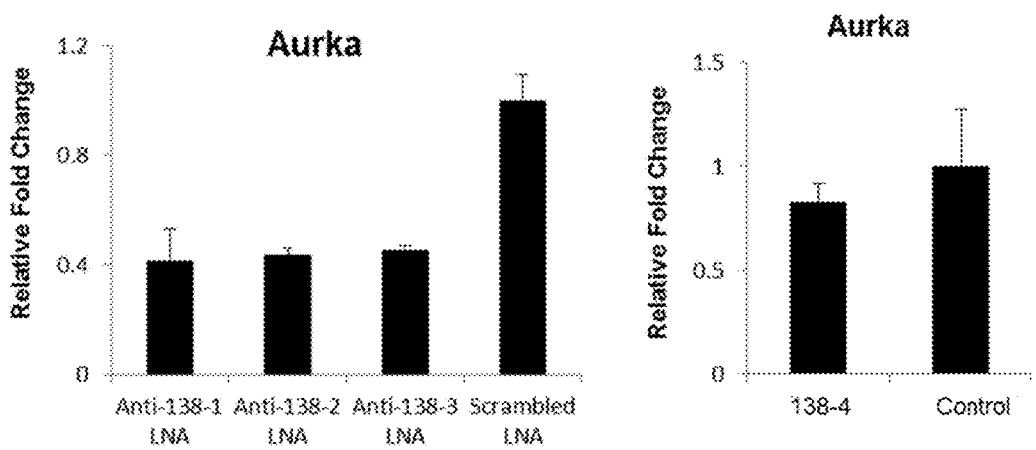
FIG. 11 shows the regulation of AURKA gene (aurora kinase A gene) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13), and anti-miR-138-4 (SEQ ID NO; 7 or "Oligo-4" or "138-4" or AMO_138_11_cap_PS) significantly down-regulates AURKA gene.
Figure 12:
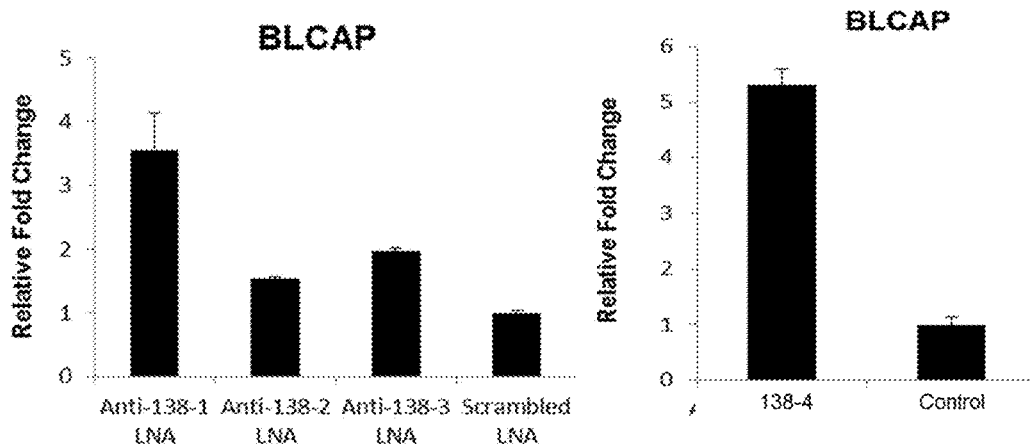
FIG. 12 shows the regulation of BLCAP gene (bladder cancer associated protein gene) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13), and anti-miR-138-4 (SEQ ID NO; 7 or "Oligo-4" or "138-4" or AMO_138_11_cap_PS) significantly up-regulates BLCAP gene.
Figure 13:
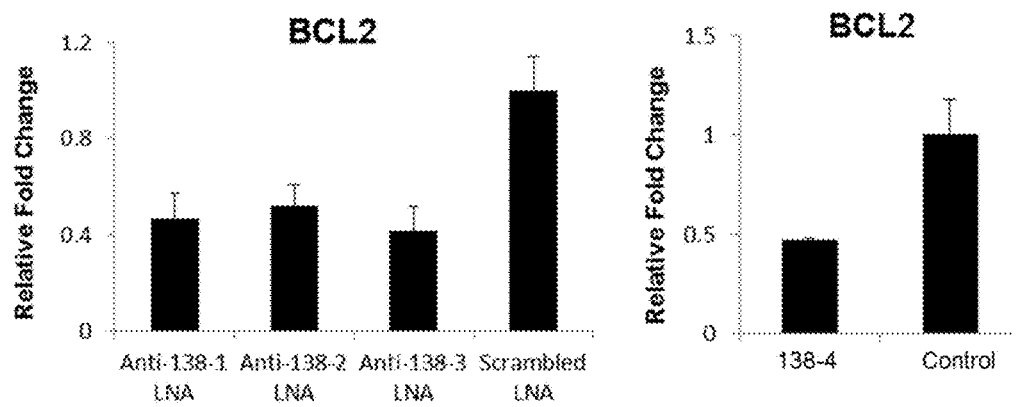
FIG. 13 shows the indirect regulation of BCL2 gene (B-cell CLL/lymphoma 2 gene) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13) and anti-miR-138-4 (SEQ ID NO; 7 or "Oligo-4" or "138-4" or AMO_138_11_cap_PS) significantly down-regulates BCL2 gene.
Figure 14:
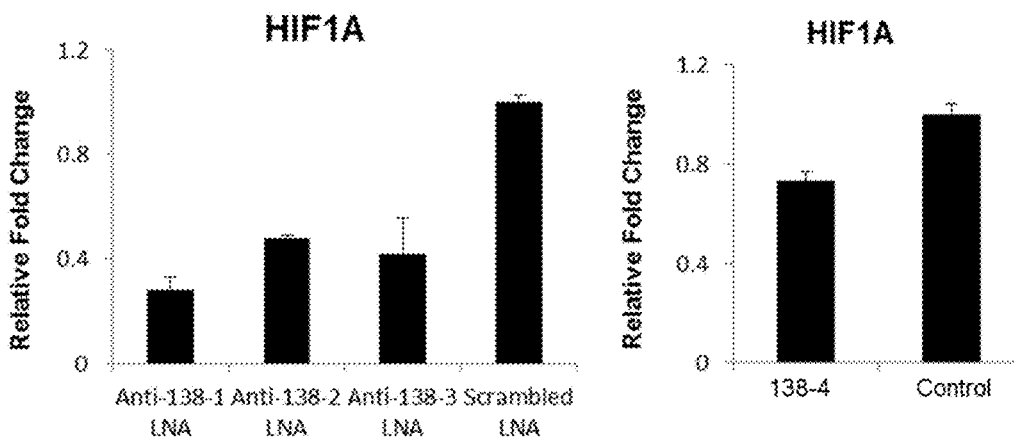
FIG. 14 shows the indirect regulation of HIF1A gene (hypoxia inducible factor 1 alpha gene) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13) and anti-miR-138-4 (SEQ ID NO; 7 or "Oligo-4" or "138-4" or AMO_138_11_cap_PS) significantly down-regulates HIF1A gene.
Figure 15:
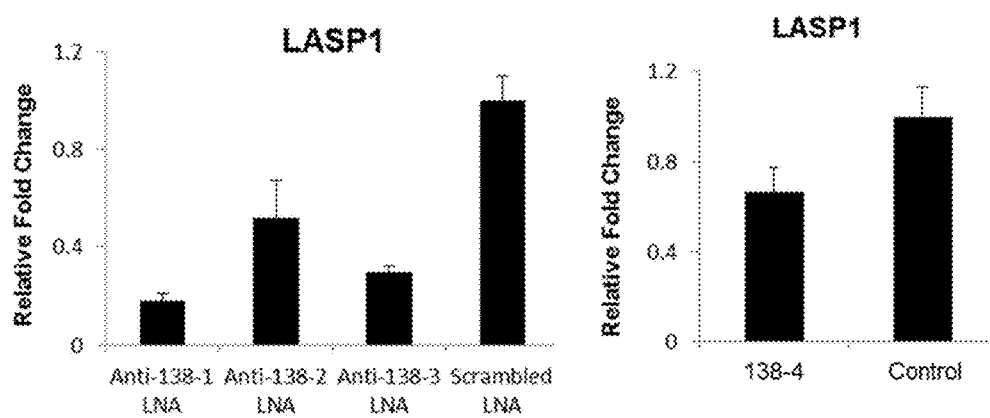
FIG. 15 shows the indirect regulation of LASP1 gene (LIM and SH3 domain protein gene) expression by anti-miR-138 oligonucleotides. As compared to the two non-targeting controls, anti-miR-138-1 (SEQ ID NO: 10), anti-miR-138-2 (SEQ ID NO: 12), anti-miR-138-3 (SEQ ID NO: 13) and anti-miR-138-4 (SEQ ID NO; 7 or "Oligo-4" or "138-4" or AMO_138_11_cap_PS) significantly down-regulates LASP1 gene.
Figure 16:
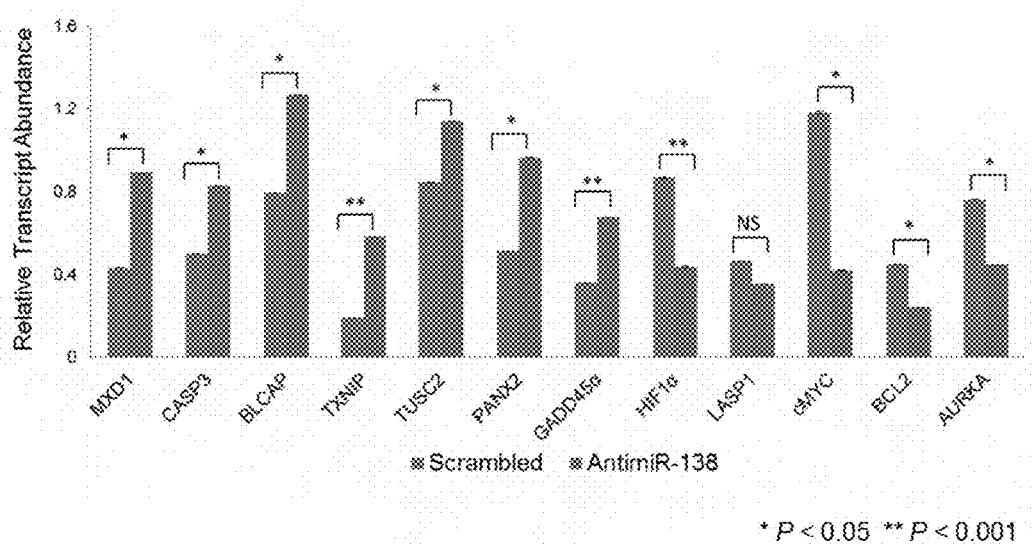
FIG. 16 shows the regulation of various genes expression by anti-miR-138-3 oligonucleotide. Genes significantly regulated by anti-miR-138-3 oligonucleotides are MXD1, CASP3, BLCAP, TXNIP, TUSC2, PANX2, GADD45α, HIF1α, LASP1, cMYC, BCL2, and AURKA. Regulation of miR-138 expression with anti-miR-138-3 oligonucleotide (i.e. SEQ ID NO: 13) is compared with scrambled control. *$P<0.05$ and $P<0.001$. Thus.

As shown in the Example section, in particular FIG. 1, FIG. 2, and FIG. 3, when exemplary oligonucleotides as described herein are transformed into a cell, the oligonucleotides could regulate the expression of miR138. However, transformation of the oligonucleotides into the cells would render the oligonucleotide to be in contact with degrading cellular enzymes. Hence, in one example, the oligonucleotides as described herein may further comprise a modification that resists degradation by cellular enzymes. For example, nuclease resistance is also improved by backbone modification of the parent phosphodiester linkages into phosphorothioate linkages (PS) in which a sulfur atom replaces one of the non-bridging oxygen atoms in the phosphate group. Thus, in one example, the oligonucleotide as described herein may be further modified with at least one phosphorothioate link.

As used herein, the term "phosphorothioate link" or "phosphorothioate linkage" refers to an inter-nucleotide linkage comprising a sulfur atom in place of a non-bridging oxygen atom within the phosphate linkages of a sugar phosphate backbone. The term "phosphorothioate link" or "phosphorothioate linkage" includes both phosphorothioate intra-nucleotide linkages and phosphorodithioate inter-nucleotide linkages. The phosphorothioate link advantageously confers the oligonucleotide its nuclease resistance properties. As used herein, the term "nuclease resistance" refers to the property of the oligonucleotide as described herein that confers resistance to digestion in the 3' to 5' direction by nuclease. Modification that may confer oligonucleotides such nuclease resistance includes, but is not limited to, modification of the phosphorothioate and boronophosphate linkages.

In one example, the modification with at least one phosphorothioate link may maintain nuclease resistance without causing the oligonucleotide to become toxic towards cells. In one example, only the 5' end and 3' end of the oligonucleotide may be modified with phosrphorothioate link. That is the phosphorothioate link modification may be provided as a cap to each end of the oligonucleotide as described herein. Thus, in one example, the middle portion of the oligonucleotide as described herein may not be modified with phosphorothioate link. In one example, the middle portion of the oligonucleotide as described herein may be phosphorothioate link-free. In one example, the oligonucleotide as described herein may have from one, or two, or three, or four, or five, or six phosphorothioate links. In one example, the phosphorothioate link may not be comprised in all of the nucleic acids of the oligonucleotide. In one example, some of the nucleic acid(s) of the oligonucleotide may be phosphorothioate link free. In one example, the modified oligonucleotide as described herein may not have phosphorothioate link on all of its nucleotide. In one example, the modified oligonucleotide as described herein may have or at least six, or at least seven, or at least eight, or at least nine, or at least 10, or at least 11, or at least 12, or at least 13, or at least 14, or at least 15, or at least 16, or at least 17, or at least 18 nucleotide(s) that are free of phosphorothioate link modification.

In one example, the phosphorothioate links may be comprised independently of each other, at least at 1, and/or at least at 2, and/or at least at 3, of the 3' end and/or 5' end of the oligonucleotide. In one example, the phosphorothioate links may be comprised independently of each other, at least at 1, and/or at least at 2 of the 3' end and/or 5' end of the oligonucleotide. In one example, the phosphorothioate links may be independently selected from positions 1 to 5 or 19 to 23 of a 23 nucleotide long anti-miR138, such as SEQ ID NO: 2. That is, assuming an anti-miR138 is 23 nucleotides in length, the phosphorothioate links may be independently selected from position 1, or 2, or 3, or 4, or 5, or 19, or 20, or 21, or 22, or 23 of a 23 nucleotide long anti-miR138, such as SEQ ID NO: 2. When the anti-miR138 is 23 nucleotides in length, in one example, the phosphorothioate links may be at positions 1, 2, 3, 20, 21 and 22 of the oligonucleotide. When the anti-miR138 is 16 nucleotides in length, in one example, the phosphorothioate links may be at positions 1, 2, 3, 13, 14, and 15 of the oligonucleotide. When the anti-miR138 is 11 nucleotides in length, in one example, the phosphorothioate links may be at positions 1, 2, 10, and 11 of the oligonucleotide. When the anti-miR138 is SEQ ID NO: 2, in one example, the phosphorothioate links may be at positions 1, 2, 3, 20, 21 and 22 of SEQ ID NO: 2.

At the same time, the inventor of the present invention has also found that the oligonucleotides as described herein may comprise less than 23 nucleotides. In one example, where the oligonucleotide as described herein has 16 nucleotides, the oligonucleotides as described herein may have all of the nucleotides modified by a locked nucleic acid modification.

In one example, where the oligonucleotide as described herein has 11 nucleotides, the oligonucleotides as described herein may have all of the nucleotides modified by a locked nucleic acid modification. In this example, the oligonucleotide may comprise or consist of the sequence 5'-A*C*AACACCAG*C*-3' (SEQ ID NO: 5), wherein * is a phosphorothioate linkage and underlined nucleotides represent a locked nucleic acid modification.

In one example, the oligonucleotide as described herein may further comprise a modification that confers stability against base hydrolysis and nucleases. In one example, such modification may include, but is not limited to, adding 2'-O-deoxy, 2'-O-methyl, 2'-O-alkyl, 2'-halo, or 2'-fluoro to the 2-hydroxyl group of the ribose moiety of a non-locked nucleic acid. In one example, the modification may be 2'O-methyl (2'-O-Me) modification of oligonucleotide. Without wishing to be bound by theory, the inventor of the present disclosure believes 2'-O-Me and locked nucleic acid modifications of the oligonucleotides as described herein confer nuclease resistance and increase the binding affinity of antimiR oligonucleotides to their cognate miRNAs. In one example, the oligonucleotide as described herein further comprises 2'-O-methyl modification. In one example, the 2'O-methyl modification may be made at positions, 1, and/or 2, and/or 3, and/or 4, and/or 5, and/or 6, and/or 7, and/or 8, and/or 9, and/or 10, and/or 11, and/or 12, and/or 13, and/or 14, and/or 15, and/or 16, and/or 17, and/or 18, and/or 19, and/or 20, and/or 21, and/or 22, and/or 23 of a 23 nucleotides long oligonucleotide. In one example, the 2'-O-methylation modification may be present in at least half of the nucleic acid in the oligonucleotide as described herein. In one example, the 2'-O-methylation modification may be present in at least 60% of the nucleic acid in the oligonucleotide as described herein. In one example, the 2'-O-methylation modification may be present in all of the nucleic acid in the oligonucleotide as described herein. In one example, when the 2'-O-methylation modification may be present in at least 11 to all nucleic acids in the oligonucleotide as described herein. In one example, when the 2'-O-methylation modification may be present in at least 11 to 16 nucleic acids in the oligonucleotide as described herein. In one example, when the 2'-O-methylation modification may be present in 12 nucleic acids in the oligonucleotide as described herein. As would be appreciated by the skilled person in the art, the position of the modification would vary relative to the length of the oligonucleotides as well as depending on the position of the other modifications made to the oligonucleotides. For example, if a nucleotide has been modified by locked nucleic acid modification, it would not be further modified by 2'-O-methylation. In one example, half of the oligonucleotide may be modified with locked nucleic acid modification and another half was modified with 2'-O-methylation. In one example, the oligonucleotide as described herein further comprises 2'-O-methyl modification at positions 1, 2, 4, 6, 11, 13, 14, 16, 18, 20, 22, and 23 of SEQ ID NO: 2.

In one example, the oligonucleotide as described herein may be further modified by inclusion a modification that improves the cell permeability of the oligonucleotide. In one example, the modification that improves cell permeability of the oligonucleotide may be a cholesterol cap modification. In one example, the cholesterol cap modification may be at either end or both ends of the oligonucleotides. In one example, the cholesterol cap modification may be at the 5' end of the oligonucleotide. Thus, in one example, the oligonucleotide may be a cholesterol-modified oligonucleotide. Method of modifying oligonucleotides with cholesterol cap is known in the art.

In one example, the oligonucleotide as described herein may be further modified by including substitution of nucleotides. As used herein, the term "substitution" refers to the removal of at least one residue sequence and insertion of a different residue in the place of the removed residue(s). For example, in order to optimize the performance of a mutation at a given site, random mutagenesis may be conducted at the target region and the expressed anti-miR-138 variants screened for the optimal combination of desired activity. Deletions or insertions may be made in adjacent pairs; i.e., a deletion of 2 residues or insertion of 2 residues. Substitutions, deletion, insertions or any combination thereof may be combined to arrive at a final construct. Changes may be made to increase the activity of the miRNA, to increase its biological stability or half-life. All such modifications to the nucleotide sequences encoding such anti-miRNA are encompassed. Techniques for making substitution mutations at predetermined sites in DNA having a known sequence are well known.

In one example, the oligonucleotide as described herein may have at least 75% sequence identity to SEQ ID NO: 2 or SEQ ID NO: 3. In one example, the oligonucleotide as described herein may have at least 80% sequence identity to SEQ ID NO: 2 or SEQ ID NO: 3. In one example, the oligonucleotide as described herein may have at least 85% sequence identity to SEQ ID NO: 2 or SEQ ID NO: 3. In one example, the oligonucleotide as described herein may have at least 90% sequence identity to SEQ ID NO: 2 or SEQ ID NO: 3. In one example, the oligonucleotide as described herein may have at least 95% sequence identity to SEQ ID NO: 2 or SEQ ID NO: 3. In one example, the oligonucleotide as described herein may have at least 97.5% sequence identity to SEQ ID NO: 2 or SEQ ID NO: 3. In one example, the oligonucleotide as described herein may have at least 99% sequence identity to SEQ ID NO: 2 or SEQ ID NO: 3. In one example, the oligonucleotide as described herein may have at least 100% sequence identity to SEQ ID NO: 2 or SEQ ID NO: 3.

In one example, the oligonucleotide as described herein may have at least 75% sequence identity to the seed/core sequence of SEQ ID NO: 2 or SEQ ID NO: 3. In one example, the oligonucleotide as described herein may have at least 80% sequence identity to the seed/core sequence of SEQ ID NO: 2 or SEQ ID NO: 3. In one example, the oligonucleotide as described herein may have at least 85% sequence identity to the seed/core sequence of SEQ ID NO: 2 or SEQ ID NO: 3. In one example, the oligonucleotide as described herein may have at least 90% sequence identity to the seed/core sequence of SEQ ID NO: 2 or SEQ ID NO: 3. In one example, the oligonucleotide as described herein may have at least 95% sequence identity to the seed/core sequence of SEQ ID NO: 2 or SEQ ID NO: 3. In one example, the oligonucleotide as described herein may have at least 97.5% sequence identity to the seed/core sequence of SEQ ID NO: 2 or SEQ ID NO: 3. In one example, the oligonucleotide as described herein may have at least 99% sequence identity to the seed/core sequence of SEQ ID NO: 2 or SEQ ID NO: 3. In one example, the oligonucleotide as described herein may have at least 100% sequence identity to the seed/core sequence of SEQ ID NO: 2 or SEQ ID NO: 3.

In one example, the oligonucleotide as described herein may comprise at least one, or at least two, or at least three, or at least four, or at least five, or six substitutions. In one example, the oligonucleotide as described herein may comprise six substitutions. In one example, the oligonucleotide as described herein may not have more than more than six, or more than seven, or more than eight, or more than nine, or more than ten, or more than 11, or more than 12, or more than 13, or more than 14, or more than 15, or more than 16, or more than 17, or more than 18, or more than 19, or more than 20, or more than 21, or more than 22, or more than 23 or all nucleotide substituted. In one example, the oligonucleotide as described herein may not have substitution that results in a complete mismatch of anti-miRNA sequence.

The inventor contemplates that changes to the sequence and each of the described chemical modifications can be varied independently. Thus, oligonucleotides as described herein of any particular length may be utilized with one or more of all the relevant chemical modifications discussed in the present disclosure.

In one example, oligonucleotide may have 40 to 60% (about 45%, or about 50%, or about 55%, or about 60%) of the nucleotides modified with locked nucleic acid modification, 40 to 60% (about 45%, or about 50%, or about 55%, or about 60%) of the non-locked nucleic acid modified nucleotides modified with 2'-O-methylation modification and 20 to 40% (about 20%, or about 25%, or about 30%, or about 35%, or about 40%) of the nucleotides are modified with phosphorothioate link modification. In one example, the oligonucleotide may contain about 5, or 6, or 7, or 8, or 9, or 10, or 11, or 12 or 13 locked nucleic acids, about 5, or 6, or 7, or 8, or 9, or 10, or 11, or 12 or 13 of the non-locked nucleic acid modified nucleotides modified with 2'-O-methylation modification and 3, or 4, or 5, or 6 of the nucleotides are modified with phosphorothioate link modification. In one example, only nucleotides at the 3'-end or 5'-end of the oligonucleotide may be modified with phosphorothioate link modification.

In one example, oligonucleotide may have about at least half of the nucleotides modified with locked nucleic acid modification, half of the non-locked nucleic acid modified nucleotides modified with 2'-O-methylation modification and about 30% of the nucleotides are modified with phosphorothioate link modification. In one example, the oligonucleotide may contain about 13 locked nucleic acids, about 13 of the non-locked nucleic acid modified nucleotides modified with 2'-O-methylation modification and 6 of the nucleotides are modified with phosphorothioate link modification. In one example, only nucleotides at the 3'-end or 5'-end of the oligonucleotide may be modified with phosphorothioate link modification.

In one example, oligonucleotide may have about 40% of the nucleotides modified with locked nucleic acid modification, 60% of the non-locked nucleic acid modified nucleotides modified with 2'-O-methylation modification and 20 to 50% (about 20%, or about 25%, or about 30%, or about 35%, or about 40%) of the nucleotides are modified with phosphorothioate link modification. In one example, the oligonucleotide may contain about 9, or 10, or 11 locked nucleic acids, about 11, or 12, or 13 of the non-locked nucleic acid modified nucleotides modified with 2'-O-methylation modification and 3, or 4, or 5, or 6 of the nucleotides are modified with phosphorothioate link modification. In one example, only nucleotides at the 3'-end or 5'-end of the oligonucleotide may be modified with phosphorothioate link modification.

In one example, oligonucleotide may have about 60% of the nucleotides modified with locked nucleic acid modification, 40% of the non-locked nucleic acid modified nucleotides modified with 2'-O-methylation modification and 20 to 50% (about 20%, or about 25%, or about 30%, or about 35%, or about 40%) of the nucleotides are modified with phosphorothioate link modification. In one example, the oligonucleotide may contain about 11, or 12, or 13 locked nucleic acids, about 9, or 10, or 11 of the non-locked nucleic acid modified nucleotides modified with 2'-O-methylation modification and 3, or 4, or 5, or 6 of the nucleotides are modified with phosphorothioate link modification. In one example, only nucleotides at the 3'-end or 5'-end of the oligonucleotide may be modified with phosphorothioate link modification.

In one example, oligonucleotide may have about 40% of the nucleotides modified with locked nucleic acid modification, 60% of the non-locked nucleic acid modified nucleotides modified with 2'-O-methylation modification and about 26% of the nucleotides are modified with phosphorothioate link modification. In one example, the oligonucleotide may contain about 9, or 10, or 11 locked nucleic acids, about 11, or 12, or 13 of the non-locked nucleic acid modified nucleotides modified with 2'-O-methylation modification and 6 of the nucleotides are modified with phosphorothioate link modification. In one example, only nucleotides at the 3'-end or 5'-end of the oligonucleotide may be modified with phosphorothioate link modification.

In one example, oligonucleotide may have about 60% of the nucleotides modified with locked nucleic acid modification, 40% of the non-locked nucleic acid modified nucleotides modified with 2'-O-methylation modification and about 26% of the nucleotides are modified with phosphorothioate link modification. In one example, the oligonucleotide may contain about 11, or 12, or 13 locked nucleic acids, about 9, 10, or 11 of the non-locked nucleic acid modified nucleotides modified with 2'-O-methylation modification and 6 of the nucleotides are modified with phosphorothioate link modification. In one example, only nucleotides at the 3'-end or 5'-end of the oligonucleotide may be modified with phosphorothioate link modification.

In one example, oligonucleotide may have about 40% of the nucleotides modified with locked nucleic acid modification, 52% of the non-locked nucleic acid modified nucleotides modified with 2'-O-methylation modification and about 26% of the nucleotides are modified with phosphorothioate link modification. In one example, the oligonucleotide may contain about 9 locked nucleic acids, about 12 of the non-locked nucleic acid modified nucleotides modified with 2'-O-methylation modification and 6 of the nucleotides are modified with phosphorothioate link modification. In one example, only nucleotides at the 3'-end or 5'-end of the oligonucleotide may be modified with phosphorothioate link modification.

In one example, oligonucleotide may have 80 to 100% (about 80%, or about 85%, or about 90%, or about 95%, or about 97.5%, or about 99%, or about 100%) of the nucleotides modified with locked nucleic acid modification, 0 to 20% (about 0%, or about 5%, or about 10%, or about 15%, or about 20%) of the non-locked nucleic acid modified nucleotides modified with 2'-O-methylation modification and at least 10 to 55% (about 10%, or about 15%, or about 20%, or about 25%, or about 30%, or about 35%, or about 40%, or about 45%, or about 50%, or about 55%) of the nucleotides are modified with phosphorothioate link modification. In one example, the oligonucleotide may have about 45-81% (about 45%, or about 50%, or about 55%, or about 60%, or about 65%, or about 70%, or about 75%, or about 80%, or about 81%) of the nucleotides free of phosphorothioate link modification. In one example, when the oligonucleotide is 11 nucleotides in length, the oligonucleotide may contain about 8, or 9, or 10, or 11 locked nucleic acids, about 0, or 1, or 2, or 3 of the non-locked nucleic acid modified nucleotides modified with 2'-O-methylation modification and 1, or 2, or 3, or 4, or 5, or 6 of the nucleotides are modified with phosphorothioate link modification. In one example, only nucleotides at the 3'-end or 5'-end of the oligonucleotide may be modified with phosphorothioate link modification.

In one example, oligonucleotide may have 90 to 100% (about 90%, or about 95%, or about 97.5%, or about 99%, or about 100%) of the nucleotides modified with locked nucleic acid modification, 0 to 10% of the non-locked nucleic acid modified nucleotides modified with 2'-O-methylation modification and at least 15 to 40% (about 15%, or about 20%, or about 25%, or about 30%, or about 35%, or about 40%) of the nucleotides are modified with phosphorothioate link modification. In one example, the oligonucleotide may have about 50 to 65% (about 50%, or about 55%, or about 60%, or about 65%) of the nucleotides free of phosphorothioate link modification. In one example, when the oligonucleotide is 11 nucleotides in length, the oligonucleotide may contain about 10 or 11 locked nucleic acids, about 0 or 1 of the non-locked nucleic acid modified nucleotides modified with 2'-O-methylation modification and 2, or 3, or 4 of the nucleotides are modified with phosphorothioate link modification. In one example, only nucleotides at the 3'-end or 5'-end of the oligonucleotide may be modified with phosphorothioate link modification.

In one example, oligonucleotide may have about 100% of the nucleotides modified with locked nucleic acid modification, no non-locked nucleic acid modified nucleotides, and about 36% of the nucleotides are modified with phosphorothioate link modification. In one example, the oligonucleotide may have about 63% of the nucleotides free of phosphorothioate link modification. In one example, when the oligonucleotide is 11 nucleotides in length, the oligonucleotide may contain about 11 locked nucleic acids, no non-locked nucleic acid modified nucleotides, and 4 of the nucleotides are modified with phosphorothioate link modification. In one example, only nucleotides at the 3'-end or 5'-end of the oligonucleotide may be modified with phosphorothioate link modification.

In one example, oligonucleotide may have about 100% of the nucleotides modified with locked nucleic acid modification, no non-locked nucleic acid modified nucleotides, no nucleotides modified with 2'-O-methylation modification, and about 36% of the nucleotides are modified with phosphorothioate link modification. In one example, when the oligonucleotide is 11 nucleotides in length, the oligonucleotide may contain about 11 locked nucleic acids, no non-locked nucleic acid modified nucleotides, no nucleotide modified with 2'-O-methylation modification, and 4 of the nucleotides are modified with phosphorothioate link modification. In one example, only nucleotides at the 3'-end or 5'-end of the oligonucleotide may be modified with phosphorothioate link modification.

In one example, oligonucleotide may have 50 to 100% (about 50%, or about 55%, or about 60%, or about 65%, or about 70%, or about 75%, or about 80%, or about 85% or about 90%, or about 95%, or about 97.5%, or about 99%, or about 100%) of the nucleotides modified with locked nucleic acid modification, 0 to 50% (about 0%, or about 5%, or about 10%, or about 15%, or about 20%, or about 25%, or about 30%, or about 35%, or about 40%, or about 45%, or about 50%) of the non-locked nucleic acid modified nucleotides modified with 2'-O-methylation modification and about 6 to 50% (about 6%, or about 10%, or about 15%, or about 20%, or about 25%, or about 30%, or about 35%, or about 40%, or about 45%, or about 50%) of the nucleotides are modified with phosphorothioate link modification. In one example, when the oligonucleotide is 16 nucleotides in length, the oligonucleotide may contain about 8, or 9, or 10, or 11, or 12, or 13, or 14, or 15, or 16 locked nucleic acids, about 0, or 1, or 2, or 3, or 4, or 5, or 6, or 7, or 8 of the non-locked nucleic acid modified nucleotides modified with 2'-O-methylation modification and 1, or 2, or 3, or 4, or 5, or 6, or 7, or 8 of the nucleotides are modified with phosphorothioate link modification. In one example, only nucleotides at the 3'-end or 5'-end of the oligonucleotide may be modified with phosphorothioate link modification.

In one example, oligonucleotide may have 75 to 100% (about 75%, or about 80%, or about 85% or about 90%, or about 95%, or about 97.5%, or about 99%, or about 100%) of the nucleotides modified with locked nucleic acid modification, 0 to 25% (about 0%, or about 5%, or about 10%, or about 15%, or about 20%, or about 25%) of the non-locked nucleic acid modified nucleotides modified with 2'-O-methylation modification and at least 10 to 40% (about 10%, or about 15%, or about 20%, or about 25%, or about 30%, or about 35%, or about 40%) of the nucleotides are modified with phosphorothioate link modification. In one example, when the oligonucleotide is 16 nucleotides in length, the oligonucleotide may contain about 12, or 13, or 14, or 15, or 16 locked nucleic acids, about 0, or 1, or 2, or 3, or 4 of the non-locked nucleic acid modified nucleotides modified with 2'-O-methylation modification and 2, or 3, or 4, or 6 of the nucleotides are modified with phosphorothioate link modification. In one example, only nucleotides at the 3'-end or 5'-end of the oligonucleotide may be modified with phosphorothioate link modification.

In one example, oligonucleotide may have about 100% of the nucleotides modified with locked nucleic acid modification, no non-locked nucleic acid modified nucleotides, and about 25% of the nucleotides are modified with phosphorothioate link modification. In one example, when the oligonucleotide is 16 nucleotides in length, the oligonucleotide may contain about 16 locked nucleic acids, no non-locked nucleic acid modified nucleotides, and 4 of the nucleotides are modified with phosphorothioate link modification. In one example, only nucleotides at the 3'-end or 5'-end of the oligonucleotide may be modified with phosphorothioate link modification.

In one example, oligonucleotide may have about 100% of the nucleotides modified with locked nucleic acid modification, no non-locked nucleic acid modified nucleotides, no nucleotides modified with 2'-O-methylation modification, and about 25% of the nucleotides are modified with phosphorothioate link modification. In one example, when the oligonucleotide is 16 nucleotides in length, the oligonucleotide may contain about 16 locked nucleic acids, no non-locked nucleic acid modified nucleotides, no nucleotide modified with 2'-O-methylation modification, and 4 of the nucleotides are modified with phosphorothioate link modification. In one example, only nucleotides at the 3'-end or 5'-end of the oligonucleotide may be modified with phosphorothioate link modification.

In one example, oligonucleotide may have 20 to 50% (about 20%, or about 25%, or about 30%, or about 35%, or about 40%, or about 45%, or about 50%) of the nucleotides modified with locked nucleic acid modification, 50 to 80% (about 50%, or about 55%, or about 60%, or about 65%, or about 70%, or about 75%, or about 80%) of the non-locked nucleic acid modified nucleotides modified with 2'-O-methylation modification and 5 to 50% (about 5%, or about 10%, or about 15%, or about 20%, or about 25%, or about 30%, or about 35%, or about 40%, or about 45%, or about 50%) of the nucleotides are modified with phosphorothioate link modification. In one example, the oligonucleotide may have about 50-95% (about 50%, or about 55%, or about 60%, or about 65%, or about 70%, or about 75%, or about 80%, or about 85%, or about 90%, or about 95%) of the nucleotides free of phosphorothioate link modification. In one example, when the oligonucleotide is 23 nucleotides in length, the oligonucleotide may contain about 4, or 5, or 6, or 7, or 8, or 9, or 10, or 11, or 12 locked nucleic acids, about 11, or 12, or 13, or 14, or 15, or 16, or 17, or 18, or 19 of the non-locked nucleic acid modified nucleotides modified with 2'-O-methylation modification and 1, or 2, or 3, or 4, or 5, or 6, or 7, or 8, or 9, or 10 of the nucleotides are modified with phosphorothioate link modification. In one example, only nucleotides at the 3'-end or 5'-end of the oligonucleotide may be modified with phosphorothioate link modification.

In one example, oligonucleotide may have 25 to 45% (about 25%, or about 30%, or about 35%, or about 40%, or about 45%) of the nucleotides modified with locked nucleic acid modification, 55 to 75% (about 50%, or about 55%, or about 60%, or about 65%, or about 70%, or about 75%) of the non-locked nucleic acid modified nucleotides modified with 2'-O-methylation modification and at least 8 to 35% (about 8%, or about 10%, or about 15%, or about 20%, or about 25%, or about 30%, or about 35%) of the nucleotides are modified with phosphorothioate link modification. In one example, the oligonucleotide may have about 65-92% (about 65%, or about 70%, or about 75%, or about 80%, or about 85%, or about 90%, or about 92%) of the nucleotides free of phosphorothioate link modification. In one example, when the oligonucleotide is 23 nucleotides in length, the oligonucleotide may contain about 5, or 6, or 7, or 8, or 9, or 10, or 11 locked nucleic acids, about 12, or 13, or 14, or 15, or 16, or 17, or 18 of the non-locked nucleic acid modified nucleotides modified with 2'-O-methylation modification and 2, or 3, or 4, or 5, or 6 of the nucleotides are modified with phosphorothioate link modification. In one example, only nucleotides at the 3'-end or 5'-end of the oligonucleotide may be modified with phosphorothioate link modification.

In one example, oligonucleotide may have about 26 to 40% (about 26%, or about 30%, or about 35%, or about 40%) of the nucleotides modified with locked nucleic acid modification, about 60 to 70% (about 60%, or about 65%, or about 70%) of the nucleotides are non-locked nucleic acid modified with 2'-O-methylation modification, and about 26% of the nucleotides are modified with phosphorothioate link modification. In one example, the oligonucleotide may have about 74% of the nucleotides free of phosphorothioate link modification. In one example, when the oligonucleotide is 23 nucleotides in length, the oligonucleotide may contain about 6, or 7, or 8, or 9 locked nucleic acids, 14, or 15, or 16 non-locked nucleic acids modified with 2'-O-methylation modification, and 6 of the nucleotides are modified with phosphorothioate link modification. In one example, only nucleotides at the 3'-end or 5'-end of the oligonucleotide may be modified with phosphorothioate link modification.

In one example, oligonucleotide may have about 40% of the nucleotides modified with locked nucleic acid modification, about 60% of the nucleotides are non-locked nucleic acid modified with 2'-O-methylation modification, and about 26% of the nucleotides are modified with phosphorothioate link modification. In one example, the oligonucleotide may have about 74% of the nucleotides free of phosphorothioate link modification. In one example, when the oligonucleotide is 23 nucleotides in length, the oligonucleotide may contain 9 locked nucleic acids, 14 non-locked nucleic acids modified with 2'-O-methylation modification, and 6 of the nucleotides are modified with phosphorothioate link modification. In one example, only nucleotides at the 3'-end or 5'-end of the oligonucleotide may be modified with phosphorothioate link modification.

In one example, oligonucleotide may have about 30% of the nucleotides modified with locked nucleic acid modification, about 70% of the nucleotides are non-locked nucleic acid modified with 2'-O-methylation modification, and about 26% of the nucleotides are modified with phosphorothioate link modification. In one example, the oligonucleotide may have about 74% of the nucleotides free of phosphorothioate link modification. In one example, when the oligonucleotide is 23 nucleotides in length, the oligonucleotide may contain 7 locked nucleic acids, 16 non-locked nucleic acids modified with 2'-O-methylation modification, and 6 of the nucleotides are modified with phosphorothioate link modification. In one example, only nucleotides at the 3'-end or 5'-end of the oligonucleotide may be modified with phosphorothioate link modification.

In one example, oligonucleotide may have about 26% of the nucleotides modified with locked nucleic acid modification, about 70% of the nucleotides are non-locked nucleic acid modified with 2'-O-methylation modification, and about 26% of the nucleotides are modified with phosphorothioate link modification. In one example, the oligonucleotide may have about 74% of the nucleotides free of phosphorothioate link modification. In one example, when the oligonucleotide is 23 nucleotides in length, the oligonucleotide may contain 6 locked nucleic acids, 16 non-locked nucleic acids modified with 2'-O-methylation modification, and 6 of the nucleotides are modified with phosphorothioate link modification. In one example, only nucleotides at the 3'-end or 5'-end of the oligonucleotide may be modified with phosphorothioate link modification.

As used herein, the term "about", in the context of number of nucleotides, means +/−5% of the stated value, or +/−4% of the stated value, or +/−3% of the stated value, or +/−2% of the stated value, or +/−1% of the stated value, or +/−0.5% of the stated value. As would be appreciated by the person skilled in the art, the percentages are provided as guidelines and should be interpreted as a guideline when determining the number of nucleotides. For example, about 40% of 23 nucleotide long oligonucleotide is 9.2 nucleotides. As it is not possible to have 9.2 nucleotides, the person skilled in the art would understand about 40% of 23 nucleotide long oligonucleotide is 9 nucleotides.

In one example, the oligonucleotide may comprise modifications according to the following formula: $[mm]_n$ $[mmL]_n[mL]_n[mmL]_n[mL]_n[mmL]_n[mL]_n[mm]_n$, where n may be 0, 1, 2, 3 or 4, m is a nucleotide modified to confer stability against base hydrolysis and nucleases (such as modification with 2'-O-methylation), L is a nucleotide modified with Locked Nucleic Acid modification. In one example, the oligonucleotide may further comprise phosphorothioate link modification at the 3' and 5' end of the oligonucleotide.

In one example, the oligonucleotide may comprise modification according to the following formula: $[min]_{n=1,2}$ $[mmL]_{n=1,2}$ $[mL]_{n=1,2,3}$ $[mmL]_{n=0,1,2,3,4}$ $[mL]_{n=1,2}$ $[mmL]_{n=1,2}$ $[mL]_{n=0,1}$ $[mm]_{n=0,1,2}$, where m is a nucleotide modified to confer stability against base hydrolysis and nucleases (such as modification with 2'-O-methylation), L is a nucleotide modified with Locked Nucleic Acid modification. In one example, the oligonucleotide may further comprise phosphorothioate link modification at the 3' and 5' end of the oligonucleotide.

In one example, the oligonucleotide may comprise modification according to the following formula: $[mm]_{n=0,1,2}$ $[mmL]_{n=1,2}$ $[mL]_{n=0,1,2}$ $[mmL]_{n=1,2}$ $[mL]_{n=0,1,2,3,4}$ $[mmL]_{n=1,2}$ $[mL]_{n=0,1,2,3,4}$ $[mm]_{n=1,2}$, m is a nucleotide modified to confer stability against base hydrolysis and nucleases (such as modification with 2'-O-methylation), L is a nucleotide modified with Locked Nucleic Acid modification. In one example, the oligonucleotide may further comprise phosphorothioate link modification at the 3' and 5' end of the oligonucleotide.

In one example, the oligonucleotide may comprise modification according to the following formula: $[mm]_{n=0,1,2}$ $[mmL]_{n=1,2}$ $[mL]_{n=0,1,2}$ $[mmL]_{n=1,2}$ $[mL]_{n=0,1,2,3,4}$ $[mmL]_{n=1,2}$ $[mL]_{n=0,1,2,3,4}$ $[mm]_{n=1,2}$, m is a nucleotide modified to confer stability against base hydrolysis and nucleases (such as modification with 2'-O-methylation), L is a nucleotide modified with Locked Nucleic Acid modification. In one example, the oligonucleotide may further comprise phosphorothioate link modification at the 3' and 5' end of the oligonucleotide.

When the modifications as described above are combined together, the modified oligonucleotides as described herein may include, but are not limited to, 5'-mC*mG*G* mCCmUmGAmUTmCAmCmAAmCAmCCmA*G*mC* mU-3' (SEQ ID NO: 13), 5'-mC*mG*G*mCmCTmGmATmUmCAmCmAAmCm ACmCmA*G*mC*mU-3' (SEQ ID NO: 12), and 5'-mC*mG*mG*mCmCTmGAmUTmCAmCAmACm ACmCmA*mG*mC*mU-3' (SEQ ID NO: 10), wherein m is a 2'-O-methylation, * is a phosphorothioate linkage and underlined nucleotides represent a locked nucleic acid modification.

As illustrated in Table 1, the oligonucleotides as described herein may have miR138 knockdown efficiency of at least 50%, or at least 60%, or at least 65%, or at least 75%, or at least 80%, or at least 85%, or at least 90%, or at least 95%, or 100%. In one example, the oligonucleotides as described herein may have miR138 knockdown efficiency of about 50 to 100%. In one example, the oligonucleotides as described herein may have miR138 knockdown efficiency of about 60 to 100%. In one example, the oligonucleotides as described herein may have miR138 knockdown efficiency of about 65 to 100%. In one example, the oligonucleotides as described herein may have miR138 knockdown efficiency of about 70 to 100%. In one example, the oligonucleotides as described herein may have miR138 knockdown efficiency of about 75 to 100%. In one example, the oligonucleotides as described herein may have miR138 knockdown efficiency of about 80 to 100%. In one example, the oligonucleotides as described herein may have miR138 knockdown efficiency of about 85 to 100%. In one example, the oligonucleotides as described herein may have miR138 knockdown efficiency of about 90 to 100%. In one example, the oligonucleotides as described herein may have miR138 knockdown efficiency of about 95 to 100%. In one example, the oligonucleotides as described herein may have miR138 knockdown efficiency of about 100%.

In one example, the oligonucleotide as described herein may encourage inhibition of aberrant proliferation, senescence or apoptosis. In one example, the oligonucleotide as described herein knockdown miR138 expression in cells without causing (non-specific) toxic cell death. In one example, the oligonucleotide as described herein encourages senescence and/or apoptosis in tumor or cancer cells without causing toxic cell death or necrosis.

Figure 26:
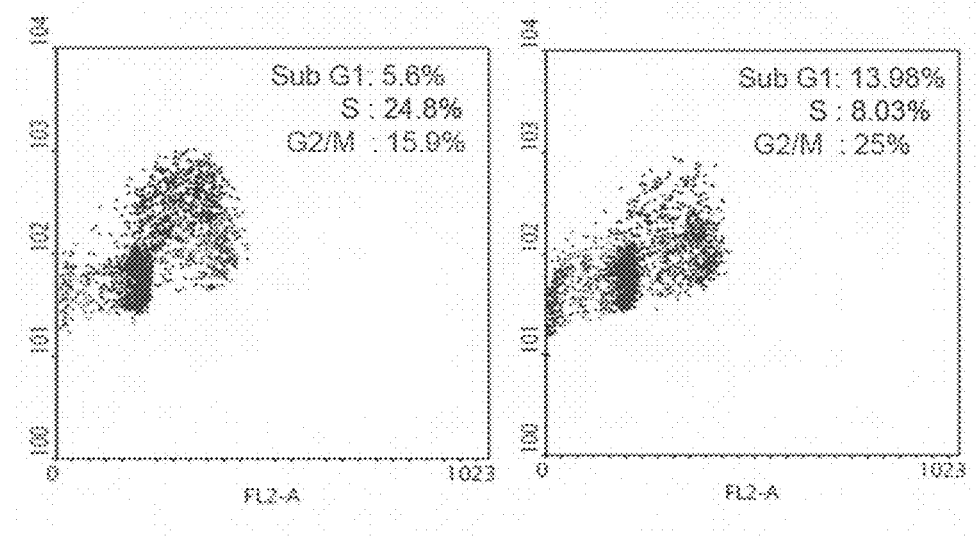
FIG. 26 shows flow cytometry results of investigation into the effect of depletion of miR-138 in breast cancer cell line. Left panel shows MDAMB231 cells (breast cancer cell line) proliferation profile after transfected with lentivirus expressing control. Cells treated with control show proliferation profile of 5.6% of cell population in Sub G1 phase, 24.8% in S phase and 15.9% in G2/M phase. Right panel shows MDAMB231 cells proliferation profile after transfected with lentivirus expressing antimiR-138. Cells treated with lentivirus expressing anti-miR-138 show proliferation profile of 13.98% in Sub G1 phase, 8.03% in S phase and 25% in G2/M phase. Thus.

As used herein, the term "senescence" refers to the permanent cessation of DNA replication and cell growth that is not reversible by growth factors. The phenomenon typically occurs at the end of the proliferative lifespan of normal cells or in tumor cells, the phenomenon may occur in response to anti-tumor or anti-cancer drugs. In one example, the phenomenon may occur after treatment with the oligonucleotides as described herein. Senescence may be characterized by certain features including, but not limited to, increased size, flattened morphology, increased granularity, and detection of senescence-associated lysosomal beta-galactosidase activity (SA-β-gal). For example, as shown in FIG. 26, senescing cells may be found to have more Sub G1 phase cells (which is a resting phase or phase before DNA replication occurs).

As used herein, the term "apoptosis" refers to the physiological process known as cell death. This process is a morphologically and biochemically distinct form of cell death that regulates cell turnover under normal physiological conditions. The morphological features include an orchestrated sequence of changes which include cell shrinkage, chromatin condensation, nuclear segmentation and eventual cellular disintegration from "budding" to discrete membrane-bound apoptotic bodies. Thus, a cell that undergoes apoptosis dies neatly, without damaging its neighbors. The biochemical features include, for example, internucleosomal cleavage of cellular DNA and the activation of ICE/Ced-3 family of proteases. This term is intended to be consistent with its use as it is known and used by those skilled in the art.

In contrast, the term "toxic cell death" or "necrosis" is used herein to refer to cell death that is triggered by external factors (such as a toxic agent, or trauma) or disease (such as infection). Toxic cell death is typically non-specific in nature. The morphological features include, but are not limited to, cell swelling, increase cell leakiness and blebbing (and in some cases bursting), and eventual disintegration in the form of cellular and nuclear lysis that can cause inflammation.

Figure 17:
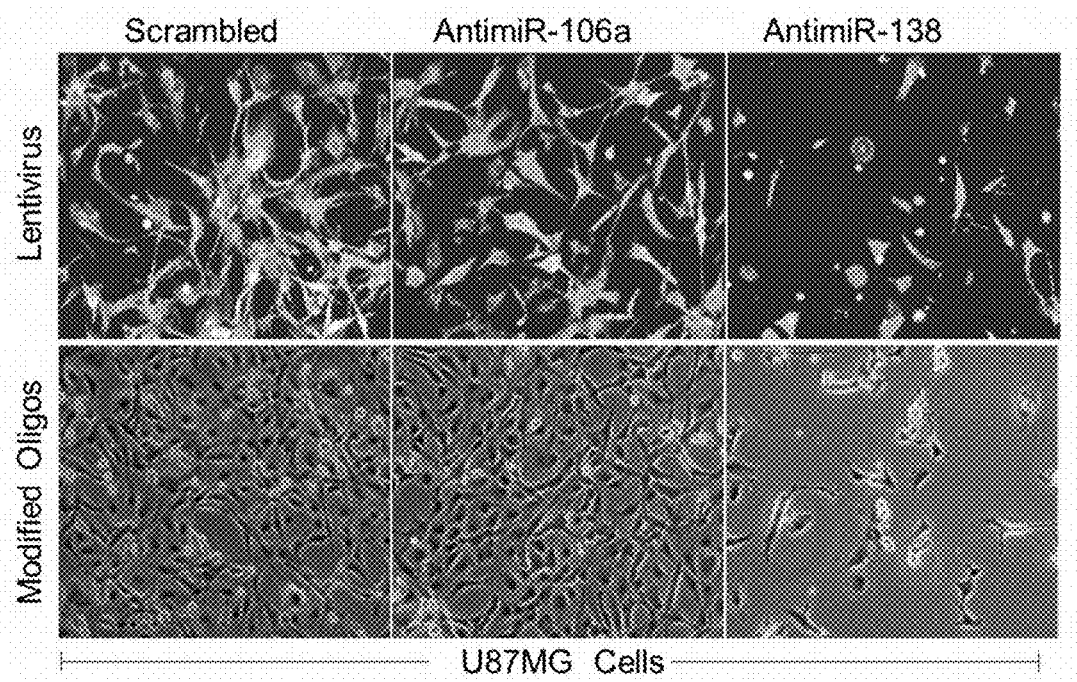
FIG. 17 shows microscopic images of U87MG cells (human glioblastoma cells) after transfection with anti-miR-138-3 oligonucleotides (SEQ ID NO: 13) or non-targeting controls (scrambled or anti-miR-106a oligonucleotides).
Figure 18:
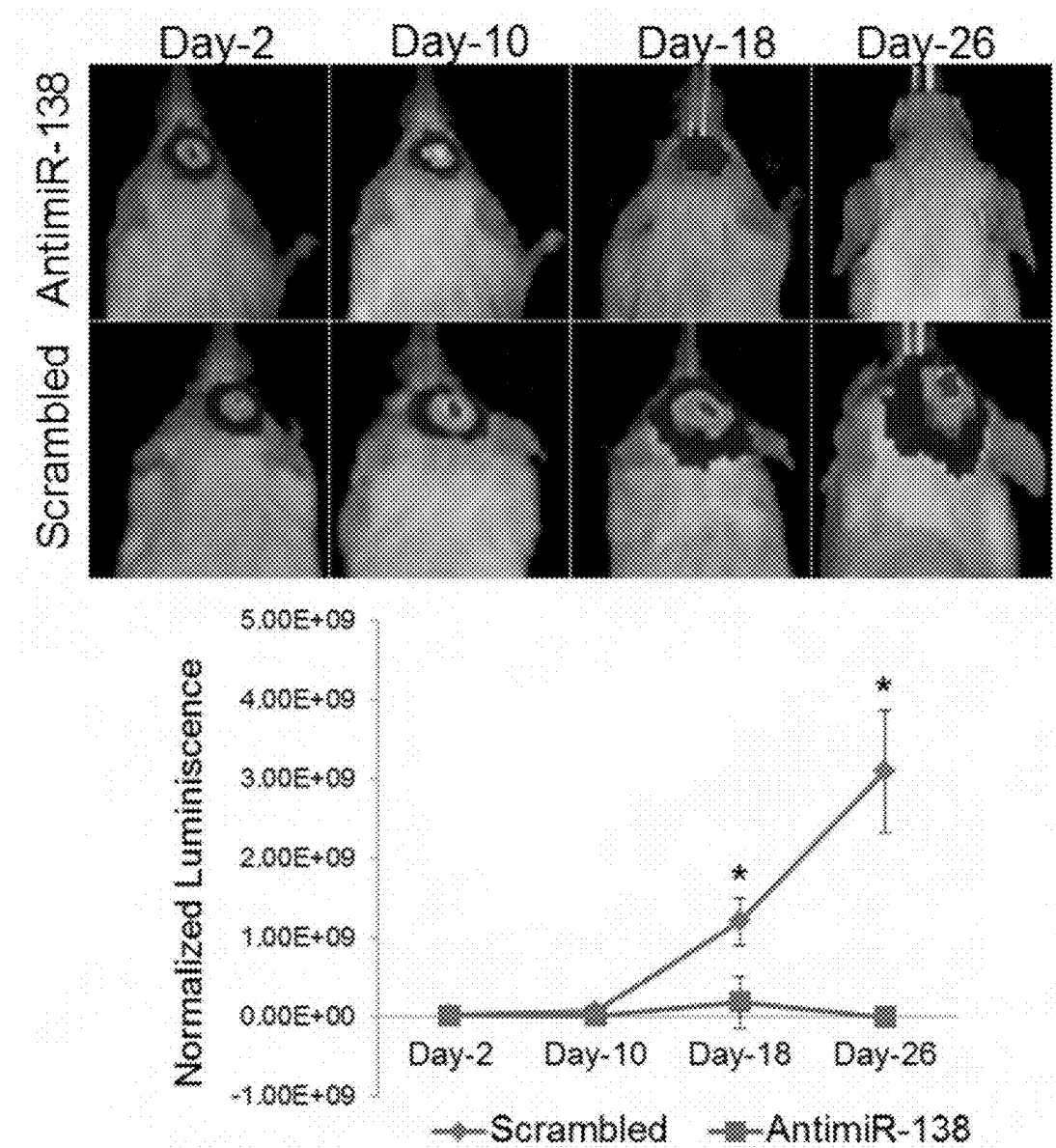
FIG. 18 shows bioluminescence imaging of U87MG glioma cells expressing luciferase in the forebrains of NOD-SCID/IL2rγ (severe-combined immunodeficient non-obese diabetic) mice at day 2, 10, 18 or 26 after implantation. Luciferase-expressing U87MG glioma cells were transfected with non-targeting control or anti-miR-138-3 (SEQ ID NO: 13) oligonucleotides before injected into the cranium of NOD-SCID/IL2rγ mice (severe-combined immunodeficient non-obese diabetic mice with interleukin 2 receptor) and maintained until development of neurological symptoms. Xenogen system for imaging was performed using IVIS spectrum Imaging System (Xenogen) and analysed using Living Image software (IVIS living image v3.0).
Figure 19:
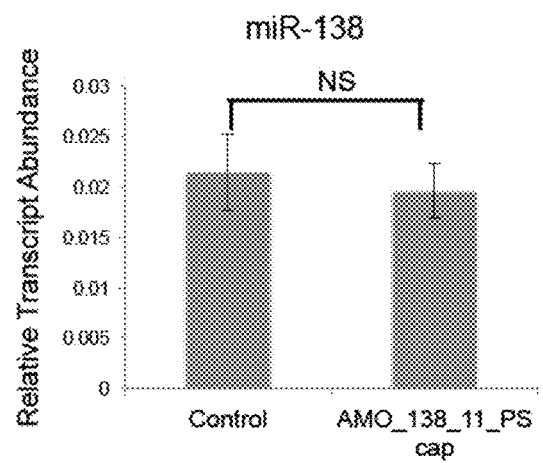
FIG. 19 shows bar graphs of the results of miRNA quantification of miR-138 levels in U87MG cell (human glioblastoma cell line). RNA was isolated from cells harvested five days after transfection with anti-miR-138 (i.e. AMO's). In particular.
Figure 20:
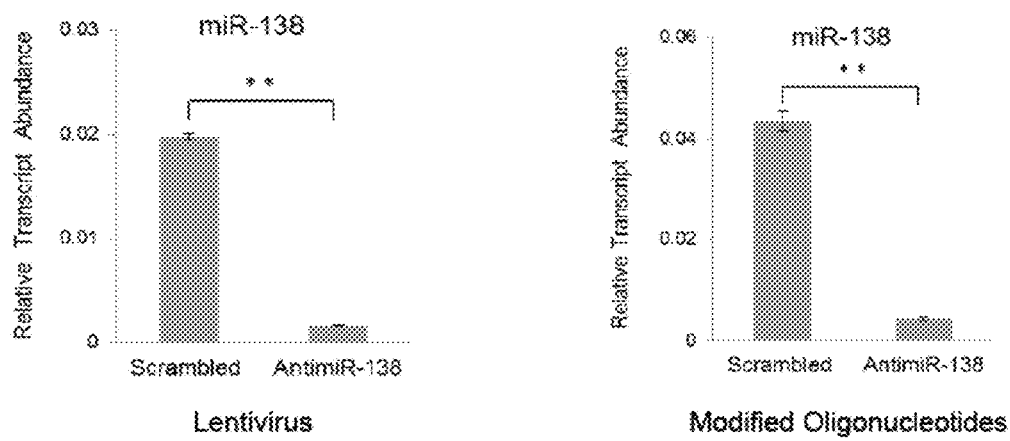
FIG. 20 shows the relative expression level of miR-138 in U87MG cells (human glioblastoma cell line) after transfection with anti-miR-138 oligonucleotides (modified 23 mer oligonucleotides). A) shows bar graph of miR-138 expression after transfection with either 23-mer oligonucleotides modified with locked nucleic acid, phosphorothioate linkage, 2'-O-methylation modifications and a cholesterol cap (i.e. AMO_138_23, 7$^{th}$ row in Table 1) or control (i.e. AMO_Control_23, 8$^{th}$ row in Table 1). Upon transfection, the level of miR-138 in cell line is significantly downregulated (A, right panel) and is comparable to downregulation after lentiviral transduction (A, left panel). B) shows light microscopic images of cells upon transfection with AMO_138_23 (7$^{th}$ row in Table 1), mismatched control (i.e. AMO_Control_23, 8$^{th}$ row in Table 1) or negative control AMO_106_23 (9$^{th}$ row in Table 1). No toxic cell death was observed and cells proliferate and grow in either culture or soft agar, forming colonies. Thus, indicating the mix of 2'O-methylation, locked nucleic acid, phosphorothioate link (at either end of oligonucleotide) and cholesterol cap modifications does not render the modified oligonucleotide to be toxic to the cells (B and C). However, cells transfected with AMO_138_23 showed significant apoptotic cell death and colony formation appears to be suppressed. Thus, indicating that depletion of miR-138 in cell lines block proliferation and induce apoptotic cell death (B and C). Anti-miR106 oligonucleotide (AMO's targeting miR-106a) was also introduced as a control. When U87MG cells (malignant glioma cell lines) were transfected with AMO_106a_23 (control, 9$^{th}$ row in Table 1), cells proliferated and formed colonies. Thus, indicating that the phenotype observe in B (far right panel) is specific only for miR-138 and the formation of any short double stranded structures do not lead to cell death or block in proliferation (FIG. 2b, 2c). Forty nanomoles of oligonucleotides were used in all experiments. Thus.
Figure 20:
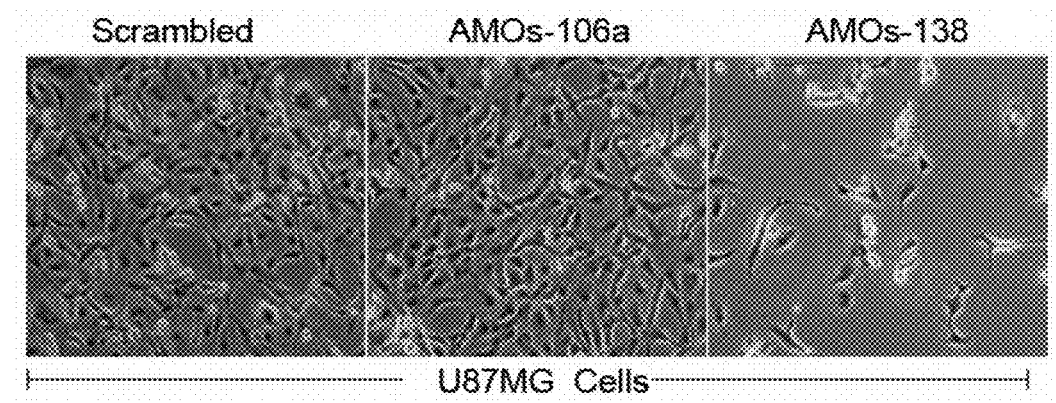
Figure 20:
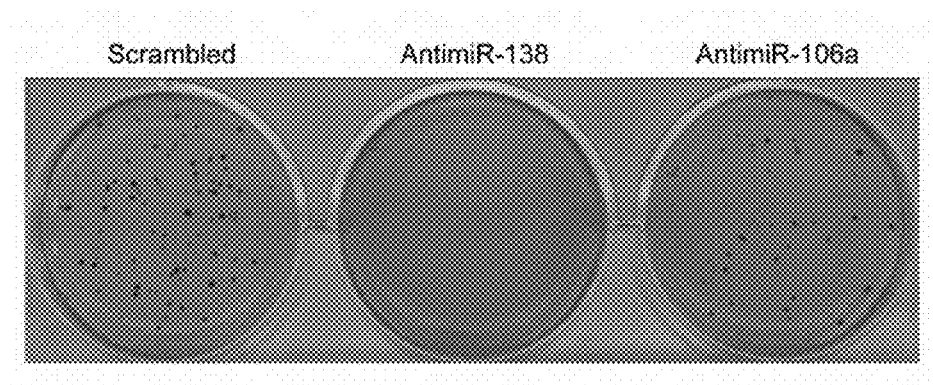
Figure 21:
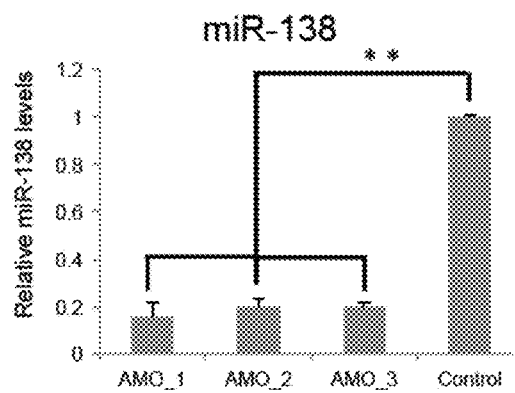
FIG. 21 shows the analysis of the effect of transducing cell lines with anti-miR-138 oligonucleotides (modified 23 mer oligonucleotides). Anti-miR-138 oligonucleotides used in FIG. 21 have locked nucleic acid, phosphorothioate linkage, and 2'-O-methylation modifications. In contrast to FIG. 20, none of the modified oligonucleotides have cholesterol cap modification. These oligonucleotides are referred to as AMO_138_23_1, AMO_138_23_2, AMO_138_23_3, and AMO_Control_23_1 (i.e. 10th, 11th, 12th and 13th row in Table 1). In all the experiments, 40 nanomoles of oligonucleotides were used. A) shows a bar graph of miR-138 expression in cell lines transfected with all three modified oligonucleotides (i.e. "AMO) and a control. It is observed that the modified anti-miR138 oligonucleotide significantly downregulates the level of miR-138 compared to the control AMOs. Cells transfected with control showed healthy growth, wherein the cells were observed to proliferate and grow in culture. No toxic cell death was observed. In contrast, cells transfected with AMO_138_23_1, AMO_138_23_2, or AMO_138_23_3 showed significant apoptotic cell death. Thus, indicating that depletion of miR-138 leads to apoptotic cell death (data not shown). B) shows an updated bar graph of the expression of GADD45a in cell lines as shown in FIG. 10 above (with multiple biological replicates). When cells are transfected with AMOs against miR-138, upregulation of GAAD45a (left panel), which is a direct target of miR-138 was observed. C) shows an updated bar graph of the expression of TXNIP in cell lines as shown in FIG. 5 above (with multiple biological replicates). At the same time, downregulation of AURKA (right panel) was also observed. When cells are transduced with AMOs-138, up-regulation of a metastasis suppressor, such as Thioredoxin-interacting protein (TXNIP), which is a transcriptional repressor of Cyclin A2 is clearly observed. Thus.
Figure 21:
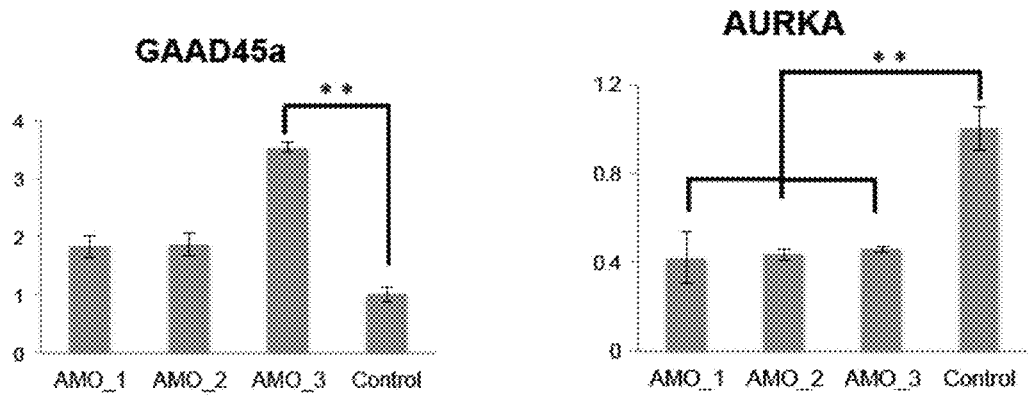
Figure 21:
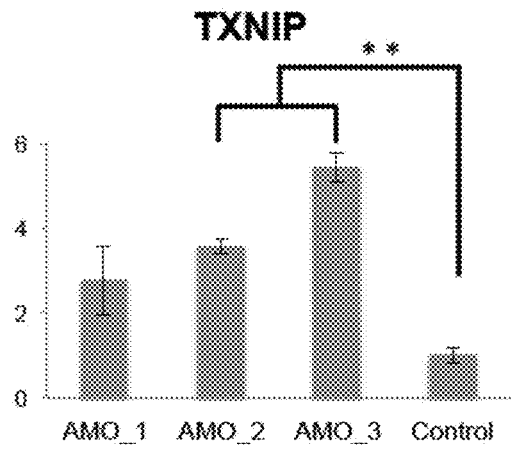
Figure 22:
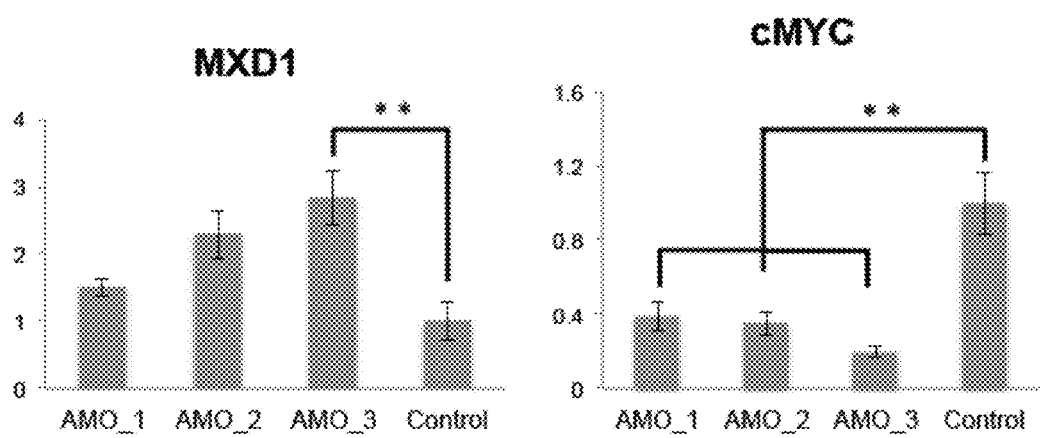
FIG. 22 shows the regulation of MXD1 gene (MAX dimerization protein 1) expression by anti-miR-138 oligonucleotides. A) shows updated bar graphs of relative expression level of two genes regulated by miR-138 as shown in FIG. 8 and FIG. 9. Left panel shows, as compared to the control, anti-miR-138-1, anti-miR-138-2, anti- and miR-138-3 up-regulates MXD1 gene. Thus, A (left panel) shows that anti-miR138-3 oligonucleotides appear to up-regulate MXD1 gene. Right panel shows the regulation of cMYC gene (v-myc avian myelocytomatosis viral oncogene homolog gene) expression by anti-miR-138 oligonucleotides. As compared to the two non-targeting controls, anti-miR-138-1, anti-miR-138-2, and anti-miR-138-3 significantly downregulates cMYC gene. Thus, A (right panel) shows a trend of better performance of cMYC regulation with anti-miR138-3 oligonucleotide. B) shows an updated bar graph (from FIG. 6 above) of relative expression level of Pannexin 2 (PANX2), which is a brain specific gap-junction protein with tumor suppressor function. As compared to the two non-targeting controls, anti-miR-138-1, anti-miR-138-2, and anti-miR-138-3 significantly up-regulates PANX2 gene.
Figure 22:
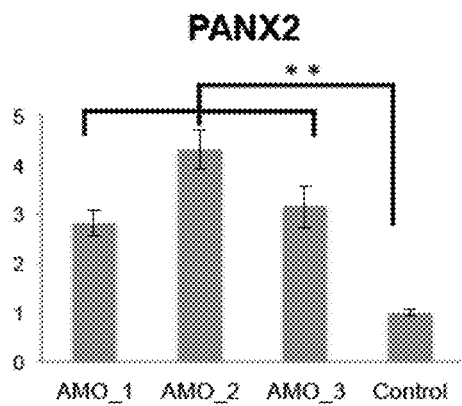
Figure 23:
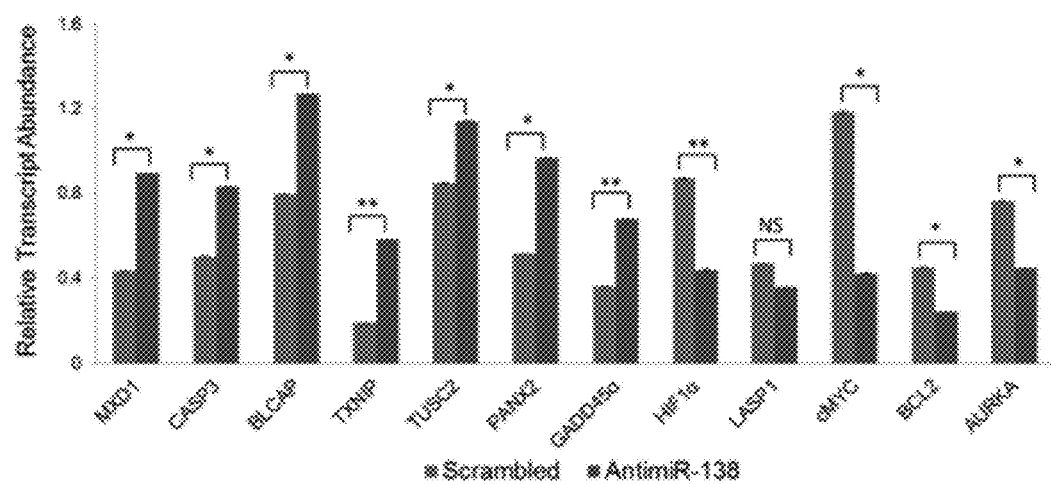
FIG. 23 shows the regulation of various genes expression by anti-miR-138 oligonucleotide. Genes significantly regulated by anti-miR-138-3 oligonucleotides are MXD1, CASP3, BLCAP, TXNIP, TUSC2, PANX2, GADD45α, HIF1α, LASP1, cMYC, BCL2, and AURKA. Regulation of miR-138 expression with modified anti-miR-138-3 oligonucleotide is compared with scrambled control. *$P<0.05$ and **$P<0.001$. Thus.
Figure 24:
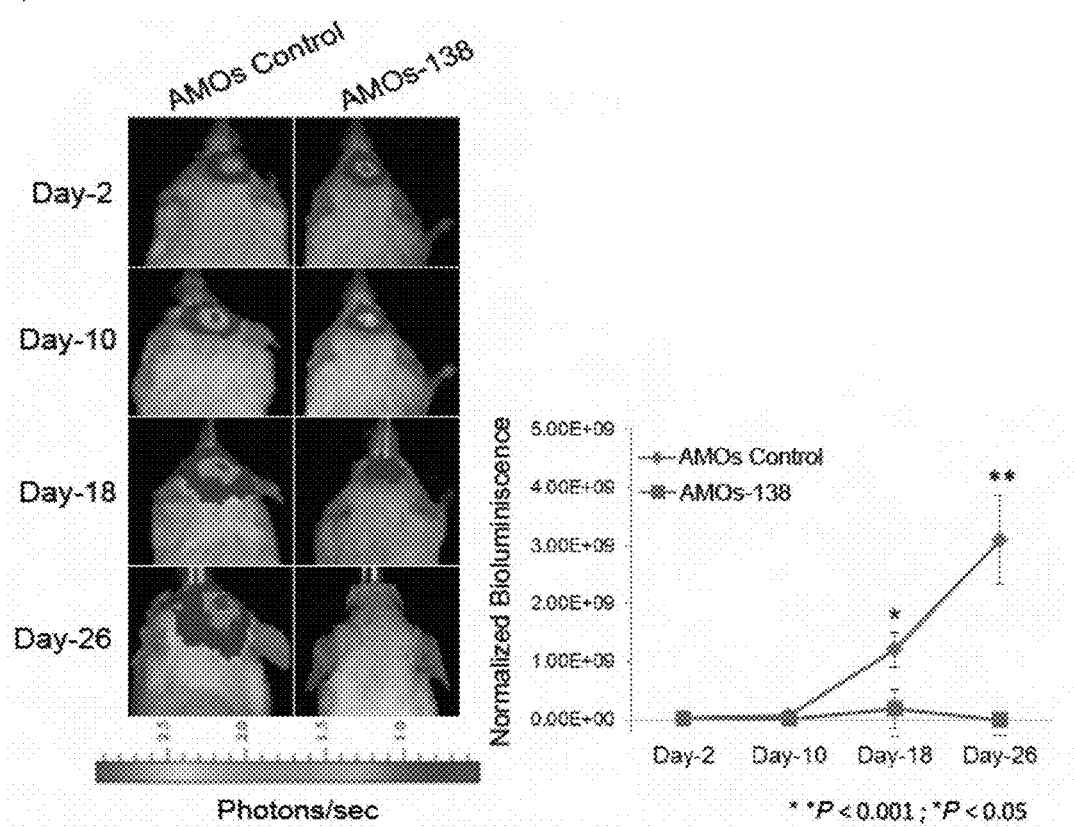
FIG. 24 shows results of studies on the effect of modified oligonucleotides in vivo. A) shows bioluminescence imaging of U87MG glioma cells expressing luciferase in the forebrains of NOD-SCID/IL2rγ (severe-combined immunodeficient non-obese diabetic with IL2rγ receptors) mice at day 2, 10, 18 or 26 after implantation with cell lines. Luciferase-expressing U87MG glioma cells were transfected with non-targeting control or modified anti-miR-138-3 oligonucleotides before intracranial injection. Xenogen system for imaging was performed using IVIS spectrum Imaging System (Xenogen) and analyzed using Living Image software (IVIS living image v3.0). Figure at left panel shows U87MG cells transfected with modified anti-miR-138-3 oligonucleotide (i.e. AMO_138_23_3, in Table 1) fail to form intracranial tumors. By day 26, no luciferase positive cells were detected in mice injected with U87MG transformed with anti-miR-138-3 oligonucleotides (i.e. AMO_138_23_3, in Table 1). In contrast, U87MG cells transfected with control anti-miR grew linearly from day 10 to day 26 post-injection. Thus, FIG. 24A (left panel) shows transfection of anti-miR138 (i.e. AMO_138_23_3, in Table 1) can inhibit the growth of glioma cells in vivo. Quantification of bioluminescence represented in FIG. 24A (right panel). (*P<0.05 and **P<0.001). B) shows photographic images of the sub-cutaneous tumor mass where the tumors were injected with control or anti-miR138 oligonucleotides (i.e. AMO_138_23_3, in Table 1). Here U87MG glioma cells were injected on either side of the flank region sub-cutaneously. Anti-miR138 oligonucleotides (i.e. AMO_138_23_3, in Table 1) or control were injected directly into the tumors on day 21. A significant inhibition in growth and reduction in tumor mass was observed on day 32 in tumor treated with anti-miR138 oligonucleotides (i.e. AMO_138_23_3, in Table 1). Quantification of bioluminescence represented in line graph under photographic images (*P<0.05 and **P<0.001).
Figure 24:
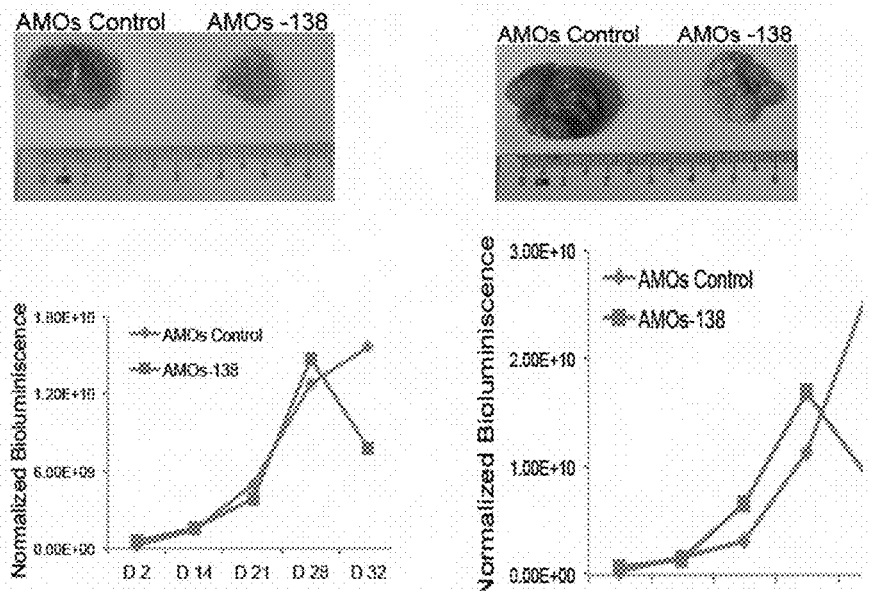

As illustrated in the Example section, for example FIG. 1, FIG. 17 and FIG. 18, the oligonucleotides as described herein can be used to reduce the proliferation of tumor cells. Thus, it will be recognized that the oligonucleotides as described herein may be used in a pharmaceutical (therapeutic) formulations. Thus, in another example, there is provided the oligonucleotide as described herein for use in medicine. The design of the oligonucleotide as described herein would require fine-tuning of various parameters such as affinity/specificity, stability in biological fluids, cellular uptake, mode of action, pharmacokinetic properties and toxicity. It is appreciated that such fine-tunings would be within the skill of a person of the art.

In yet another example there is provided a pharmaceutical composition comprising an effective amount of the oligonucleotide as described herein, or a pharmaceutically-acceptable salt thereof, and a pharmaceutically-acceptable carrier or diluent. In one example, the oligonucleotides as described herein may be used "as is" or in the form of a variety of pharmaceutically acceptable salts. As used herein, the term "pharmaceutically acceptable salts" refers to salts that retain the desired biological activity of the oligonucleotides as described herein and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N'-dibenzylethylene-diamine, D-glucosamine, tetraethylammonium, or ethylenediamine. In one example, the oligonucleotide may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach.

In one example, the pharmaceutical compositions may include, but are not limited to, solutions, emulsions, and liposome-containing formulations. These compositions may be generated from a variety of components that include, but are not limited to, preformed liquids, self-emulsifying solids and self-emulsifying semisolids. Delivery of oligonucleotides or pharmaceutical compositions as described herein to tumour tissue may be enhanced by carrier-mediated delivery including, but not limited to, cationic liposomes, cyclodextrins, porphyrin derivatives, branched chain dendrimers, polyethylen-imine polymers, nanoparticles and microspheres. The pharmaceutical formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions as described herein may be formulated into any of many possible dosage forms such as, but not limited to, tablets, capsules, gel capsules, liquid syrups, soft gels and suppositories. The compositions as described herein may also be formulated as suspensions in aqueous, non-aqueous or mixed media. Aqueous suspensions may further contain substances, which increase the viscosity of the suspension including, for example, sodium carboxymethyl-cellulose, sorbitol and/or dextran. The suspension may also contain stabilizers. The compositions as described herein may also be conjugated to active drug substances, for example, aspirin, ibuprofen, a sulfa drug, an antidiabetic, an antibacterial or an antibiotic. In one example, the pharmaceutical composition may further comprise a pharmaceutically acceptable adjuvant. In one example, the pharmaceutically acceptable carrier may include, but is not limited to, a colloidal dispersion system, macromolecular complex, nanocapsule, microsphere, bead, oil-in-water emulsion, micelle, mixed micelle, or liposome. In one example, the pharmaceutically acceptable carrier or diluent may comprise or consist of saline.

In another example, there is provided a method of treating a proliferative disease in a subject in need thereof. The method comprises administering the oligonucleotide as described herein into the subject. As used herein, the term "treating" or "treatment" of a proliferative condition, disease, or syndrome includes (i) inhibiting the proliferative disease, disorder, or syndrome, i.e. arresting its development of tumor/cancer; and/or (ii) relieving the proliferative disease, disorder, or syndrome, i.e. causing regression of the proliferative disease, disorder or syndrome.

In one example, the proliferative disease may include, but is not limited to, a benign tumor or cancer. In one example, the proliferative disease may be cancer. In one example, the cancer may be brain cancer and/or breast cancer. In one example, the cancer may be brain cancer. In one example, the brain cancer may include, but is not limited to, anaplastic astrocytoma, anaplastic mixed glioma, anaplastic oligoastrocytoma, anaplastic oligodendroglioma, germinoma, glioblastoma multiforme, gliosarcoma, low grade astrocytoma, low grade mixed oligoastrocytoma, low grade oligodendroglioma, central nervous system lymphoma, meduloblastoma, meningioma, pilocytic astrocytoma, acoustic neuroma, chordoma, craniopharyngioma, brain stem glioma, ependymoma, optic nerve glioma, subependymoma, metastatic brain tumors, pituitary tumors, primitive neuroectodermal and scwannoma. In one example, the cancer may be glioma, such as malignant glioma and benign glioma. In one example, the glioma may include, but is not limited to, astrocytoma (glioblastoma multiforme), brainstem glioma, ependymoma, mixed glioma, oligodendroglioma, optic nerve glioma, and the like.

Figure 25:
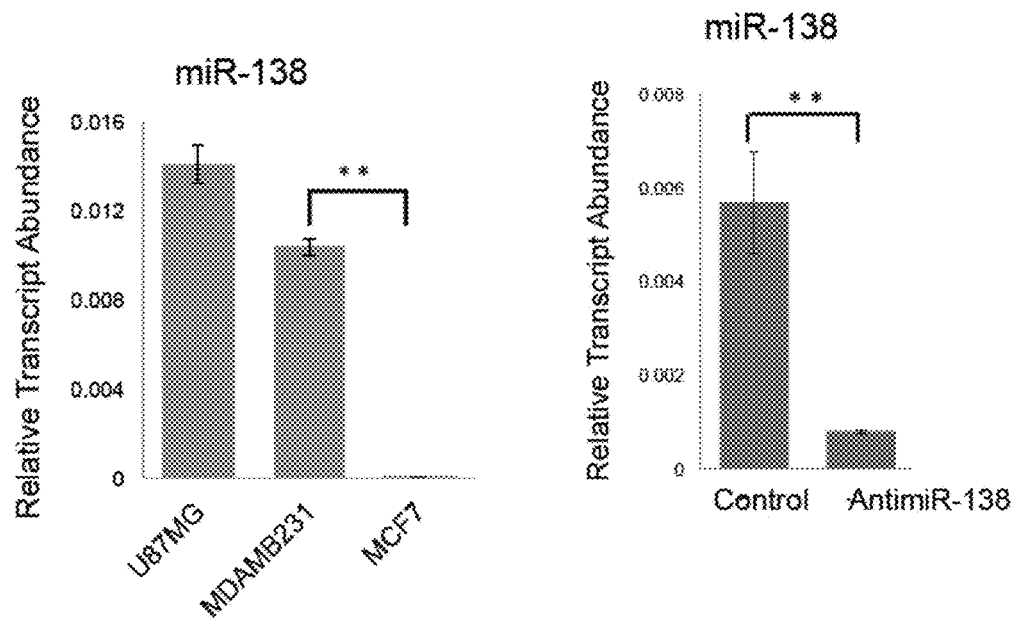
FIG. 25 shows the relative expression level of miR-138 in U87MG cells (human glioblastoma cell line), MDAMB231 cells (breast cancer cell line), and MCF7 cells (breast cancer cell line) after depleted of miR138 using anti-miR-138. Left panel shows miR-138 depletion in MDAMB231 using lentivirus-based anti-miRs for knockdown. Thus.
Figure 27:
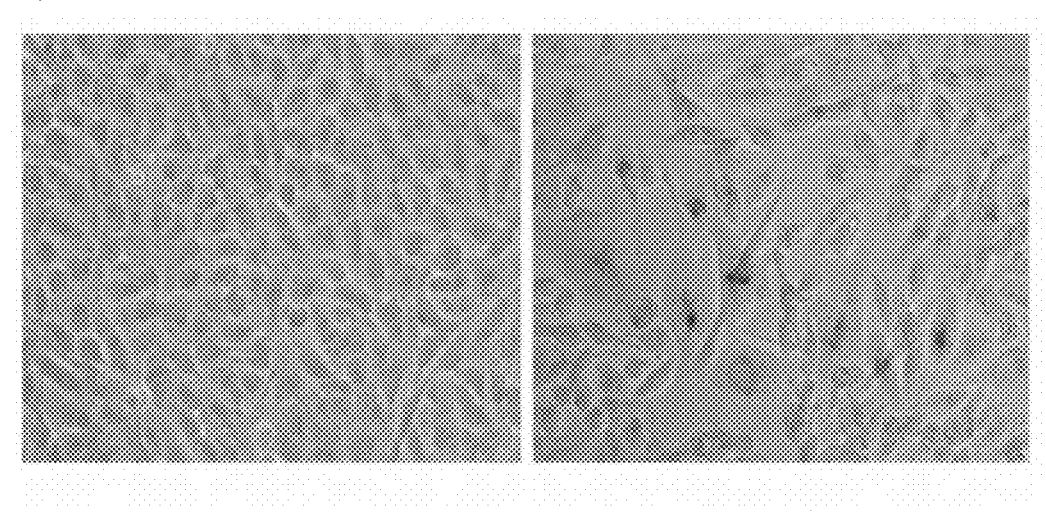
FIG. 27 shows light microscopic images of MDAMB231 cells (breast cancer cell lines) depleted of miR-138 using lentivirus expressing anti-miR-138. In particular, left panel shows cells transfected with control lentivirus and right panel transfected with lentivirus expressing antimiR-138. Left panel shows cells grow to confluency; Right panel shows signs of apoptotic cell death and senescence. Right panel also shows dark spots indicating accumulation of endogenous lysosomal beta galactosidase, which is typically observed in senescent cells. Thus, showing anti-miR-138 oligonucleotide can prevent the proliferation of breast cancer cell lines and encourage cells to senesce.

As shown in FIGS. 25 to 27, depletion of miR138 in breast cancer cells prevents cell proliferation and encouraged senescence. Thus, in one example, in one example, an agent that reduces miR-138 expression in breast cancer may be used to treat breast cancer. In one example, the cancer may be breast cancer. In one example, the breast cancer may be luminal breast cancer, ductal carcinoma in situ breast cancer, invasive (or infiltrating) ductal carcinoma (including tubular carcinoma of the breast, medullary carcinoma of the breast, papillary carcinoma of the breast, cribriform carcinoma of the breast), invasive (or infiltrating) lobular carcinoma, inflammatory breast cancer, Paget disease of the nipple, male breast cancer, Phyllodes tumor, angiosarcoma, adenoid cystic carcinoma, low grade adenosquamous carcinoma, medullary carcinoma, mucinous (or colloid) carcinoma, papillary carcinoma, tubular carcinoma, metaplastic carcinoma (such as spindle cell and squamous carcinoma), micropapillary carcinoma, mixed carcinoma (has features of both invasive ductal and lobular), recurrent and metastatic breast cancer and the like.

The oligonucleotides disclosed herein are useful for a number of therapeutic applications as indicated above. In general, therapeutic methods as described herein may include administration of a therapeutically effective amount of the oligonucleotide as described herein to a subject. As used herein, the term "subject" may include any mammal, such as human. As used herein, the term "administering", "administration", "administered" refers to methods of administering the oligonucleotides or pharmaceutical compositions as described herein in to a subject. In one example, administering or administration may include administration in many ways, including, topically, parenterally, intravenously, intradermally, intramuscularly, colonically, rectally, or intraperitoneally. In one example, the administration may be parenteral administration. In one example, the parenteral administration may include, but is not limited to intravenous, subcutaneous, intraperitoneal, or intramuscular. In one example, the oligonucleotide as described herein or pharmaceutical composition as described herein may be administered by oral, transdermal, sustained release, controlled release, delayed release, suppository, catheter, or sublingual administration.

In one example, the method comprising administration of the oligonucleotides as described herein may further comprise administering a second therapeutic agent (e.g., a chemotherapeutic agent) to the subject.

In one example, the pharmaceutical composition as described herein may comprise the oligonucleotide as described herein. In one example, the pharmaceutical composition may further comprise a second therapeutic agent.

In one example, the second therapeutic agent may be an anti-cancer agent, such as trastuzumab, capecitabine, bevacizumab, and taxanes. In one example, the second therapeutic agent may include, but is not limited to, trastuzumab, capecitabine, bevacizumab, paclitaxel, docetaxel and the likes. In one example, the second agent may be administered prior to, concurrently, separately or subsequently of the oligonucleotide as described herein.

In one example, the method as described herein, or the pharmaceutical composition as described herein, or the oligonucleotide as described herein, may be provided prior to or after other treatment of cancer (such as brain or breast cancer). In one example, the other treatment of cancer (such as brain cancer) may include, but is not limited to, surgery, radiation therapy and chemotherapy or mixtures thereof.

In one example, the previous treatment for brain cancer may include, but is not limited to, surgery, conventional external radiation therapy, three-dimensional conformal radiation therapy, intensity modulated radiation therapy, stereotactic radiosurgery, fractionated stereotactic radiation therapy, proton radiation therapy, internal or implant radiation therapy, temozolomide, bevacizumab, carmustine, lomustine, procarbazine, vincristine, tumor treating fields therapy, everolimus, procarbazine, lomustine, cisplatin, carboplatin and methotrexate or mixtures thereof.

In one example, the previous treatment for breast cancer may include, but is not limited to, surgery, sentinel lymph node biopsy followed by surgery, radiation therapy, chemotherapy, hormone therapy and targeted therapy. In one example, the previous treatment for breast cancer may include, but is not limited to, lumpectomy, partial mastectomy, segmental mastectomy, total mastectomy, modified radical mastectomy, external radiation, internal radiation, ado-trastuzumab emtansine, anastrozole, bevacizumab, capecitabine, carboplatin, cyclophosphamide, darbepoetin alfa, daunorubicin, denosumab, docetaxel, doxorubicin, epirubicin, epoetin alfa, eribulin, everolimus, exemestane, filgrastim, fluorouracil, fluoxymesterone, fulvestrant, gemcitabine, goserelin, ixabepilone, lapatinib, letrozole, leucovorin, leuprolide, megestrol, methotrexate, mitoxantrone, mutamycin, paclitaxel, paclitaxel albumin-stabilized nanoparticle formulation, pamidronate, pegfilgrastim, pertuzumab, raloxifene, tamoxifen, thiotepa, toremifene, trastuzumab, trastuzumab emtansine, triptorelin, vincristine, vinorelbine and zoledronic acid or mixtures thereof. In certain embodiments, the previous treatment for breast cancer is selected from bevacizumab, capecitabine, carboplatin, cyclophosphamide, daunorubicin, docetaxel, doxorubicin, epirubicin, eribulin, everolimus, fluorouracil, gemcitabine, ixabepilone, methotrexate, mitoxantrone, mutamycin, paclitaxel, paclitaxel albumin-stabilized nanoparticle formulation, tamoxifen, trastuzumab, trastuzumab emtansine, vincristine and vinorelbine or mixtures thereof.

In another example, there is provided the use of an oligonucleotide as described herein in the manufacture of a medicament for treating a proliferative disease in a subject in need thereof.

In one example, there is also provided a method of reducing or inhibiting the activity of miR-138 in a cell comprising contacting the cell with the oligonucleotide as described herein. In one example, the cell may be a mammalian cell. In one example, the cell may be a glial cell. In one example, the cell may be in vitro, in vivo or ex vivo.

In one example, the pharmaceutical compositions as described herein may further comprise one or more chemotherapeutic agents. When used with the oligonucleotides or pharmaceutical compositions as described herein, such chemotherapeutic agents may be used individually, sequentially, or in combination with one or more other such chemotherapeutic agents or in combination with radiotherapy. All chemotherapeutic agents known to a person skilled in the art are here incorporated as combination treatments with oligonucleotides or pharmaceutical compositions as described herein. Other active agents, such as anti-inflammatory drugs, including but not limited to non-steroidal anti-inflammatory drugs and corticosteroids, antiviral drugs, and immuno-modulating drugs may also be combined with the oligonucleotides or pharmaceutical compositions as described herein.

The oligonucleotide as described herein may also be provided as a kit. The kit may be for administering the oligonucleotide to a subject for treating and/or diagnosing a disease state. In one example, the kit may include two or more components necessary for treating and/or diagnosing the disease state, such as a cancerous condition. Components may include oligonucleotide as described herein, the pharmaceutical composition as described herein, reagents, containers and/or equipment. In one example, the container within the kit may contain an oligonucleotide as described herein including a radiopharmaceutical that is radiolabeled before use. The kits may further include any of the reaction components or buffer necessary for administering the oligonucleotide as described herein. Moreover, the oligonucleotide as described herein may be in lyophilized form and then reconstituted prior to administration.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Material and Methods

Cell Culture: U87MG cell lines are cultured in MEM media (Gibco) supplemented with 10% FBS, sodium pyruvate (Gibco), L-glutamate (Gibco) and Pen-Strep (Gibco) in a 5% $CO^2$ incubator maintained at 37° C. Cells were passaged at 75% confluency using 0.25% Trypsin (Gibco).

Transfection with anti-sense oligos (ASO's): 100,000 U87MG cells were seeded in 6 well plates followed by transfection with 40 nano moles of ASO. The ASO's with multiple modifications were developed to target microRNA-138 and were also referred to as anti-miR-138-1 (SEQ ID NO: 10), anti-miR-138-2 (SEQ ID NO: 12), anti-miR-138-3 (SEQ ID NO: 13) or antimiR-138-4 (SEQ ID NO: 5, or "oligo-4") along with two non-targeting controls. Subsequent to the second round of transfection with 40 nano moles of ASO, cells were split into 60 mm dishes (cells from 2 wells are split into five 60 mm dishes). Microscopic images were taken each day for 7 days continuously to study their phenotype. Latter cells were harvested for RNA isolation.

Anti-miR-138 sequences are as follows:

TABLE 1

Sequences of anti-miR-138 oligonucleotides, showing knockdown efficiency and phenotype of cells treated with the anti-miR-138 oligonucleotides.

| SEQ ID NO: | Name of anti-miR138 oligonucleotides (i.e. AMO) | Length (nts) | Sequence | Modification | Knockdown Efficiency | Phenotype of U87MG cells after treatment with AMO |
| --- | --- | --- | --- | --- | --- | --- |
| 5 | AMO_138_11_Cap_PS or anti-miR138-4 | 11 | A*C*AACACCAG*C* | Complete LNA + 2 nts PS at each 5' and 3' ends | miR-138 ~15-25% | No significant cell death |
| 6 | AMO_Control_11_Cap_PS | 11 | C*A*AACACCGA*C* | Complete LNA + 2 nts PS at each 5' and 3' end | miR-138 0% | AMOs are less toxic |
| 7 | AMO_138_23 | 23 | mC*mG*G*mCmCTmGmATmUmCAmCmAAmCmACmCmA*G*mC*mU/3CholTEG/ | Mix of 2'O-methyl + LNA + PS + Cholesterol cap | miR-138 90% Targets ~60-75% | Proliferation block with significant apoptotic cell death |
| 8 | AMO_Control_23 | 23 | mG*mG*C*mAmATmCmCAmAmCGmGmACmCmUTmCmA*C*mC*mU/3CholTEG/ | Mix of 2'O-methyl + LNA + PS + Cholesterol cap | miR-138 0% Targets No Change | Cells are viable as AMOs are not toxic |
| 9 | AMO_106_23 | 23 | mC*mU*mA*mCmCTmG CmACmUGmUAmAG mCAmCmU*mU*mU* mU/3CholTEG/ | Mix of 2'O-methyl + LNA + PS + Cholesterol cap | miR-138 0% Targets No Change | Cells are viable as AMOs are not toxic |
| 10 | AMO_138_23_1 or anti-miR138-1 | 23 | mC*mG*mG*mCmCT mGAmUTmCAmCAm ACmACmCmA*mG*m C*mU | Mix of 2'O-methyl + LNA + PS | miR-138 ~85-90% Targets ~50-60% | Proliferation block with significant apoptotic cell death |

TABLE 1-continued

Sequences of anti-miR-138 oligonucleotides, showing
knockdown efficiency and phenotype of cells treated
with the anti-miR-138 oligonucleotides.

| SEQ ID NO: | Name of anti-miR138 oligonucleotides (i.e. AMO) | Length (nts) | Sequence | Modification | Knock-down Effi-ciency | Phenotype of U87MG cells after treatment with AMO |
|---|---|---|---|---|---|---|
| 11 | AMO_Control_23_1 | 23 | mG*mG*C*mAmATmCmAmAmCGmGmACmCmUTmCmA*C*mC*mU | Mix of 2'O-methyl + LNA + PS | miR-138 0% Targets No Change | Cells are viable as AMOs are not toxic |
| 12 | AMO_138_23_2 or anti-miR138-2 | 23 | mC*mG*G*mCmCTmGmATmUmCAmCmAAmCmACmCmA*G*mC*mU | Mix of 2'O-methyl + LNA + PS | miR-138 ~90% Targets ~60-75% | Proliferation block with significant apoptotic cell death |
| 13 | AMO_138_23_3 or anti-miR138-3 | 23 | mC*mG*G*mCCmUmGAmUTmCAmCmAAmCAmCCmA*G*mC*mU | Mix of 2'O-methyl + LNA + PS | miR-138 ~90-95% Targets ~70-85% | Proliferation block with significant apoptotic cell death |

Table legend:
Modifications present in Table 1 include, m is 2'O-methylation (2'OMe/2'O-methyl) modification, * is phosphorothioate linkages (PS) and/or underline is a locked nucleic acid modification (LNA).

The term "targets" refers to the relative regulation of downstream genes that are targeted by the depletion/knockdown of miR138.

RNA isolation: RNA isolation was carried out using Exiqon miRCURY™ RNA Isolation Kit following manufacturer's instructions. DNase treatment was carried out using Qiagen RNase free DNase enzyme and finally the RNA was suspended in a volume of 50 µl.

Quantification of microRNA and mRNA: Total RNA (50 ng) was reverse transcribed using miRNA specific primers (Applied Biosystems, Life Technologies, USA) according to TaqMan miRNA Reverse Transcription Kit (Life Technologies, USA). Real time analysis of the miRNA expression was carried out using TaqMan probes. Ct values of miRNAs were normalized against U6 snRNA internal control and values plotted as relative transcript abundance. Total RNA (500 ng) was reverse transcribed with Superscript III (Life Technologies, USA) and anchored oligodT primer as per the manufacturer's instructions. Transcript levels were measured by quantitative RT-PCR using SYBR green PCR master mix (Applied Biosystems, Life Technologies, USA) using gene specific primers. Ct values were normalized to endogenous ribosomal large subunit P0 (RPLP0) values. All experiments were performed in three biological replicates and representative figures are shown.

Intracranial implantation of Glioma cells: Luciferase-expressing U87MG glioma cells were transfected with non-targeting control ASOs or specific ASOs targeting miR-138. 48 hours post-transfection cells were washed with PBS and used for intracranial injections. Intracranial implantation of luciferase expressing U87MG cells into 8 weeks old NOD/SCID/IL2rγ mice (Jackson) was performed in accordance with the Institutional Animal Care and Use Committee approved protocol. $5 \times 10^4$ cells in 3 µl were injected stereotactically into the forebrain of immune-deficient mice and maintained till the development of neurological symptoms. Tumor formation/growth/regression will be measured by tracking bioluminescence or by subjecting the mice to magnetic resonance imaging (MRI).

Bioluminescence Imaging: U87MG glioma cells expressing luciferase were established by selecting for puromycin (1 µg/ml) after transducing with Lentivirus expressing Luciferase under human PGK promoter (Addgene). For bioluminescence imaging, U87MG glioma cells expressing luciferase transfected with anti-miR138 oligonucleotide (i.e. AMO's) were injected into the right forebrains of NOD-SCID mice, and Xenogen system was used for imaging. After an intraperitoneal dose of 150 mg/kg of D-luciferin, mice were anesthetized and imaging was performed using IVIS spectrum Imaging System (Xenogen). Quantification was based on total flux (photons/sec) of emitted light as a measure of the relative number of viable cells. Bioluminescence signals were analyzed using Living Image software (IVIS living image v3.0).

β-Galactosidase Staining: MDAM231 cells (breast cancer cell line) cytochemical staining for Senescence-associated di-galactosidase was performed using a Senescence β-Galactosidase Staining Kit (for example, Cell Signaling Technology, Kit #9860, USA). Representative results are shown.

Cell cycle analysis: Flow cytometric analysis by quantitation of DNA content to analyse the cell cycle progression. The single time-point measurement reveals the percentage of cells in G1 (Gap 1 phase, where cells increase in size and preparing for DNA synthesis) vs. S (Synthesis phase, where DNA replication occurs) vs. G2/M (Gap2/Mitosis phase, where G2 is when cell continues to grow and ensures all are ready for entering into M (mitosis) phase and divide; M is when cell growth stops and cellular energy is focused on the orderly division into two daughter cells). This analysis was also performed using MDAM231 cells (breast cancer cell line) transduced with lentivirus expressing antitaiR-138 or control.

What is claimed is:

1. An oligonucleotide comprising one of the sequences selected from the group consisting of 5'-mC*mG*G*mCCmUmGA mUTmCAmCmAAmC AmCCmA*G*mC*mU-3' (SEQ ID NO: 13), and 5'-mC*mG*mG*mCmCmTmGAmUTmCAmCAmACm ACmCmA*mG*mC*mU-3' (SEQ ID NO: 10), wherein m is a 2'-O-methylation, * is a phosphorothioate linkage and underlined nucleotides represent a locked nucleic acid modification.

2. The oligonucleotide of claim 1, wherein the locked nucleic acid creates a bi-cyclic structure that locks the conformation of the ribose, optionally the bi-cyclic structure is created by ribose moiety modification which creates a bridge connecting 2' oxygen to 4' carbon, optionally the bridge is an ethylene, methylene or oxy-methylene bridge.

3. A pharmaceutical composition comprising an effective amount of an oligonucleotide comprising one of the sequences selected from the group consisting of 5'-mC*mG*G*mCCmUmGA mUTmCAmCmAAmC AmCCmA*G*mC*mU-3' (SEQ ID NO: 13), and 5'-mC*mG*mG*mCmCmTmGAmUTmCAmCAmACmAC mCmA*mG*mC*mU-3' (SEQ ID NO: 10), wherein m is a 2'-O-methylation, * is a phosphorothioate linkage and underlined nucleotides represent a locked nucleic acid modification, or a pharmaceutically-acceptable salt thereof, and a pharmaceutically-acceptable carrier or diluent.

* * * * *